US009343923B2

(12) United States Patent
Joshi

(10) Patent No.: US 9,343,923 B2
(45) Date of Patent: May 17, 2016

(54) IMPLANTABLE MEDICAL DEVICE WITH BACKSCATTER SIGNAL BASED COMMUNICATION

(75) Inventor: Himanshu Joshi, Houston, TX (US)

(73) Assignee: CYBERONICS, INC., Houston, TX (US)

(*) Notice: Subject to any disclaimer, the term of this patent is extended or adjusted under 35 U.S.C. 154(b) by 709 days.

(21) Appl. No.: 13/593,178

(22) Filed: Aug. 23, 2012

(65) Prior Publication Data

US 2014/0055088 A1 Feb. 27, 2014

(51) Int. Cl.
*H02J 7/00* (2006.01)
*H02J 7/02* (2016.01)
*A61N 1/372* (2006.01)
*H02J 5/00* (2016.01)
*A61N 1/378* (2006.01)

(52) U.S. Cl.
CPC .............. *H02J 7/025* (2013.01); *A61N 1/3727* (2013.01); *A61N 1/37229* (2013.01); *A61N 1/3787* (2013.01); *H02J 5/005* (2013.01)

(58) Field of Classification Search
CPC ...... G07C 5/008; G07C 5/085; G07C 5/0808; G07C 1/22; G06K 19/0717; B60N 2/2863; B60C 23/041; B60C 23/0408; B60C 23/0433; B60C 11/24; B60C 23/008; B60C 23/0496; B60R 21/20; B60R 21/233
USPC .................................................. 320/106–112
See application file for complete search history.

(56) References Cited

U.S. PATENT DOCUMENTS

| | | |
|---|---|---|
| 3,195,540 A | 7/1965 | Waller |
| 3,764,748 A | 10/1973 | Branch et al. |
| 4,014,346 A | 3/1977 | Brownlee et al. |
| 4,925,443 A | 5/1990 | Heilman et al. |
| 5,279,292 A | 1/1994 | Baumann et al. |
| 5,290,227 A | 3/1994 | Pasque |
| 5,350,413 A | 9/1994 | Miller |
| 5,411,537 A | 5/1995 | Munshi et al. |
| 5,569,156 A | 10/1996 | Mussivand |
| 5,591,217 A | 1/1997 | Barreras |
| 5,630,836 A | 5/1997 | Prem et al. |
| 5,676,162 A | 10/1997 | Larson, Jr. et al. |
| 5,676,651 A | 10/1997 | Larson, Jr. et al. |
| 5,690,693 A | 11/1997 | Wang et al. |
| 5,693,091 A | 12/1997 | Larson, Jr. et al. |
| 5,702,430 A | 12/1997 | Larson, Jr. et al. |

(Continued)

OTHER PUBLICATIONS

Lin, Tse-Yu et al., "Ultra-thin tag fabrication and sensing technique using third harmonic for implantable wireless sensors," Microwave Symposium Digest (MTT), 2011 IEEE MTT-S International, Jun. 5-10, 2011, Baltimore, MD., 4 pages.

*Primary Examiner* — Binh Tat
(74) *Attorney, Agent, or Firm* — Foley & Lardner LLP

(57) ABSTRACT

An implantable medical device is disclosed that includes a charging coil configured to inductively couple to a first external coil to receive a charging signal to charge a charge storage element of the implantable medical device. The implantable medical device also includes a circuit coupled to the charging coil. The circuit includes a circuit component that, in response to the charging signal, generates a backscatter signal. The implantable medical device also includes a communication coil orthogonal to the charging coil and coupled to the circuit component. The communication coil is configured to inductively couple to a second external coil to communicate the backscatter signal to the second external coil.

23 Claims, 6 Drawing Sheets

(56) References Cited

U.S. PATENT DOCUMENTS

| | | |
|---|---|---|
| 5,702,431 A | 12/1997 | Wang et al. |
| 5,704,891 A | 1/1998 | Mussivand |
| 5,713,939 A | 2/1998 | Nedungadi et al. |
| 5,722,930 A | 3/1998 | Larson, Jr. et al. |
| 5,733,313 A | 3/1998 | Barreras, Sr. et al. |
| 5,755,748 A | 5/1998 | Borza |
| 5,758,666 A | 6/1998 | Larson, Jr. et al. |
| 5,769,877 A | 6/1998 | Barreras |
| 5,807,397 A | 9/1998 | Barreras |
| 5,810,015 A | 9/1998 | Flaherty |
| 5,814,095 A | 9/1998 | Muller et al. |
| 5,879,375 A | 3/1999 | Larson, Jr. et al. |
| 5,945,762 A | 8/1999 | Chen et al. |
| 5,948,006 A | 9/1999 | Mann |
| 5,954,058 A | 9/1999 | Flaherty |
| 5,991,665 A | 11/1999 | Wang et al. |
| 5,995,874 A | 11/1999 | Borza |
| 6,052,624 A | 4/2000 | Mann |
| 6,058,330 A | 5/2000 | Borza |
| 6,067,474 A | 5/2000 | Schulman et al. |
| 6,067,991 A | 5/2000 | Forsell |
| 6,088,619 A | 7/2000 | Hein et al. |
| 6,092,531 A | 7/2000 | Chen et al. |
| 6,141,588 A | 10/2000 | Cox et al. |
| 6,164,284 A | 12/2000 | Schulman et al. |
| 6,166,518 A | 12/2000 | Echarri et al. |
| 6,185,452 B1 | 2/2001 | Schulman et al. |
| 6,205,359 B1 | 3/2001 | Boveja |
| 6,208,894 B1 | 3/2001 | Schulman et al. |
| 6,210,347 B1 | 4/2001 | Forsell |
| 6,212,431 B1 | 4/2001 | Hahn et al. |
| 6,227,204 B1 | 5/2001 | Baumann et al. |
| 6,240,316 B1 | 5/2001 | Richmond et al. |
| 6,240,318 B1 | 5/2001 | Phillips |
| 6,269,266 B1 | 7/2001 | Leysieffer |
| 6,272,382 B1 | 8/2001 | Faltys et al. |
| 6,275,737 B1 | 8/2001 | Mann |
| 6,278,258 B1 | 8/2001 | Echarri et al. |
| 6,308,101 B1 | 10/2001 | Faltys et al. |
| 6,315,721 B2 | 11/2001 | Schulman et al. |
| 6,321,118 B1 | 11/2001 | Hahn |
| 6,324,430 B1 | 11/2001 | Zarinetchi et al. |
| 6,324,431 B1 | 11/2001 | Zarinetchi et al. |
| 6,327,504 B1 | 12/2001 | Dolgin et al. |
| 6,331,744 B1 | 12/2001 | Chen et al. |
| 6,345,202 B2 | 2/2002 | Richmond et al. |
| 6,356,788 B2 | 3/2002 | Boveja |
| 6,366,814 B1 | 4/2002 | Boveja et al. |
| 6,368,592 B1 | 4/2002 | Colton et al. |
| 6,389,318 B1 | 5/2002 | Zarinetchi et al. |
| 6,392,386 B2 | 5/2002 | Schulmayr et al. |
| 6,393,325 B1 | 5/2002 | Mann et al. |
| 6,430,444 B1 | 8/2002 | Borza |
| 6,442,434 B1 | 8/2002 | Zarinetchi et al. |
| 6,445,162 B1 | 9/2002 | Mukainakano |
| 6,450,173 B1 | 9/2002 | Forsell |
| 6,450,946 B1 | 9/2002 | Forsell |
| 6,453,198 B1 | 9/2002 | Torgerson et al. |
| 6,453,907 B1 | 9/2002 | Forsell |
| 6,454,698 B1 | 9/2002 | Forsell |
| 6,454,699 B1 | 9/2002 | Forsell |
| 6,454,700 B1 | 9/2002 | Forsell |
| 6,454,701 B1 | 9/2002 | Forsell |
| 6,460,543 B1 | 10/2002 | Forsell |
| 6,461,292 B1 | 10/2002 | Forsell |
| 6,461,293 B1 | 10/2002 | Forsell |
| 6,463,935 B1 | 10/2002 | Forsell |
| 6,464,628 B1 | 10/2002 | Forsell |
| 6,464,655 B1 | 10/2002 | Shahinpoor |
| 6,470,892 B1 | 10/2002 | Forsell |
| 6,471,635 B1 | 10/2002 | Forsell |
| 6,475,136 B1 | 11/2002 | Forsell |
| 6,482,145 B1 | 11/2002 | Forsell |
| 6,496,733 B2 | 12/2002 | Zarinetchi et al. |
| 6,503,189 B1 | 1/2003 | Forsell |
| 6,505,074 B2 | 1/2003 | Boveja et al. |
| 6,505,077 B1 | 1/2003 | Kast et al. |
| 6,516,227 B1 | 2/2003 | Meadows et al. |
| 6,525,512 B2 | 2/2003 | Wuzik et al. |
| 6,531,847 B1 | 3/2003 | Tsukamoto et al. |
| 6,533,733 B1 | 3/2003 | Ericson et al. |
| 6,540,659 B1 | 4/2003 | Milbocker |
| 6,553,263 B1 | 4/2003 | Meadows et al. |
| 6,554,762 B2 | 4/2003 | Leysieffer |
| 6,564,102 B1 | 5/2003 | Boveja |
| 6,564,807 B1 | 5/2003 | Schulman et al. |
| 6,565,503 B2 | 5/2003 | Leysieffer et al. |
| 6,570,363 B2 | 5/2003 | Boberschmidt et al. |
| 6,575,894 B2 | 6/2003 | Leysieffer et al. |
| 6,586,912 B1 | 7/2003 | Tsukamoto et al. |
| 6,587,724 B2 | 7/2003 | Mann et al. |
| 6,592,512 B2 | 7/2003 | Stöckert et al. |
| 6,609,032 B1 | 8/2003 | Woods et al. |
| 6,611,715 B1 | 8/2003 | Boveja |
| 6,615,081 B1 | 9/2003 | Boveja |
| 6,620,094 B2 | 9/2003 | Miller |
| 6,629,923 B2 | 10/2003 | Leysieffer |
| 6,631,296 B1 | 10/2003 | Parramon et al. |
| 6,657,351 B2 | 12/2003 | Chen et al. |
| 6,664,763 B2 | 12/2003 | Echarri et al. |
| 6,668,191 B1 | 12/2003 | Boveja |
| 6,678,561 B2 | 1/2004 | Forsell |
| 6,695,885 B2 | 2/2004 | Schulman et al. |
| 6,697,674 B2 | 2/2004 | Leysieffer et al. |
| 6,709,385 B2 | 3/2004 | Forsell |
| 6,726,678 B1 | 4/2004 | Nelson et al. |
| 6,731,986 B2 | 5/2004 | Mann et al. |
| 6,736,770 B2 | 5/2004 | Leysieffer et al. |
| 6,745,077 B1 | 6/2004 | Griffith et al. |
| 6,807,445 B2 | 10/2004 | Baumann et al. |
| 6,850,803 B1 | 2/2005 | Jimenez et al. |
| 6,856,838 B2 | 2/2005 | Parramon et al. |
| 6,875,180 B2 | 4/2005 | Weiner et al. |
| 6,879,859 B1 | 4/2005 | Boveja |
| 6,891,353 B2 | 5/2005 | Tsukamoto et al. |
| 6,894,456 B2 | 5/2005 | Tsukamoto et al. |
| 6,895,280 B2 | 5/2005 | Meadows et al. |
| 6,901,290 B2 | 5/2005 | Foster et al. |
| 6,909,917 B2 | 6/2005 | Woods et al. |
| 6,915,165 B2 | 7/2005 | Forsell |
| 6,937,894 B1 | 8/2005 | Isaac et al. |
| 6,949,929 B2 | 9/2005 | Gray et al. |
| 6,954,674 B2 | 10/2005 | Connelly et al. |
| 6,979,351 B2 | 12/2005 | Forsell et al. |
| 7,001,427 B2 | 2/2006 | Aharoni et al. |
| 7,009,362 B2 | 3/2006 | Tsukamoto et al. |
| 7,011,624 B2 | 3/2006 | Forsell |
| 7,017,583 B2 | 3/2006 | Forsell |
| 7,062,330 B1 | 6/2006 | Boveja et al. |
| 7,062,331 B2 | 6/2006 | Zarinetchi et al. |
| 7,063,691 B2 | 6/2006 | Nelson et al. |
| 7,076,304 B2 | 7/2006 | Thompson |
| 7,076,307 B2 | 7/2006 | Boveja et al. |
| 7,107,103 B2 | 9/2006 | Schulman |
| 7,114,502 B2 | 10/2006 | Schulman et al. |
| 7,123,013 B2 | 10/2006 | Gray |
| 7,126,310 B1 | 10/2006 | Barron |
| 7,151,914 B2 | 12/2006 | Brewer |
| 7,155,291 B2 | 12/2006 | Zarinetchi et al. |
| 7,167,756 B1 | 1/2007 | Torgerson et al. |
| 7,177,690 B2 | 2/2007 | Woods et al. |
| 7,177,691 B2 | 2/2007 | Meadows et al. |
| 7,184,836 B1 | 2/2007 | Meadows et al. |
| 7,191,012 B2 | 3/2007 | Boveja et al. |
| 7,198,594 B2 | 4/2007 | Shahinpoor |
| 7,200,504 B1 | 4/2007 | Fister |
| 7,212,110 B1 | 5/2007 | Martin et al. |
| 7,212,864 B2 | 5/2007 | Wahlstrand et al. |
| 7,225,032 B2 | 5/2007 | Schmeling et al. |
| 7,226,442 B2 | 6/2007 | Sheppard et al. |
| 7,235,044 B2 | 6/2007 | Forsell |
| 7,239,918 B2 | 7/2007 | Strother et al. |
| 7,242,982 B2 | 7/2007 | Singhal et al. |
| 7,248,929 B2 | 7/2007 | Meadows et al. |

(56) References Cited

U.S. PATENT DOCUMENTS

| | | |
|---|---|---|
| 7,263,401 B2 | 8/2007 | Scott et al. |
| 7,283,867 B2 | 10/2007 | Strother et al. |
| 7,286,880 B2 | 10/2007 | Olson et al. |
| 7,286,881 B2 | 10/2007 | Schommer et al. |
| 7,295,878 B1 | 11/2007 | Meadows et al. |
| 7,317,947 B2 | 1/2008 | Wahlstrand et al. |
| 7,337,010 B2 | 2/2008 | Howard et al. |
| 7,367,938 B2 | 5/2008 | Forsell |
| 7,375,492 B2 * | 5/2008 | Calhoon et al. ............... 320/108 |
| 7,376,563 B2 | 5/2008 | Leysieffer et al. |
| 7,379,775 B2 | 5/2008 | Parramon et al. |
| 7,388,378 B2 | 6/2008 | Gray et al. |
| 7,392,089 B2 | 6/2008 | Wahlstrand et al. |
| 7,400,926 B2 | 7/2008 | Forsell |
| 7,426,445 B1 | 9/2008 | Fister |
| 7,444,184 B2 | 10/2008 | Boveja et al. |
| 7,460,911 B2 | 12/2008 | Cosendai et al. |
| 7,486,048 B2 | 2/2009 | Tsukamoto et al. |
| 7,496,404 B2 | 2/2009 | Meadows et al. |
| 7,499,753 B2 | 3/2009 | Forsell |
| 7,505,816 B2 | 3/2009 | Schmeling et al. |
| 7,513,257 B2 | 4/2009 | Schulman et al. |
| 7,515,967 B2 | 4/2009 | Phillips et al. |
| 7,529,586 B2 | 5/2009 | Wahlstrand et al. |
| 7,532,933 B2 | 5/2009 | Hastings et al. |
| 7,555,346 B1 | 6/2009 | Woods et al. |
| 7,592,776 B2 | 9/2009 | Tsukamoto et al. |
| 7,596,408 B2 | 9/2009 | Singhal et al. |
| 7,621,863 B2 | 11/2009 | Forsell |
| 7,621,878 B2 | 11/2009 | Ericson et al. |
| 7,635,541 B2 | 12/2009 | Scott et al. |
| 7,647,109 B2 | 1/2010 | Hastings et al. |
| 7,648,455 B2 | 1/2010 | Forsell |
| 7,666,132 B2 | 2/2010 | Forsell |
| 7,671,594 B2 | 3/2010 | Gray |
| 7,682,745 B2 | 3/2010 | Howard et al. |
| 7,684,867 B2 | 3/2010 | Jaax et al. |
| 7,720,546 B2 | 5/2010 | Ginggen et al. |
| 7,727,277 B2 | 6/2010 | Aharoni et al. |
| 7,729,777 B2 | 6/2010 | Gray et al. |
| 7,736,390 B2 | 6/2010 | Aharoni et al. |
| 7,738,965 B2 | 6/2010 | Phillips et al. |
| 7,765,003 B2 | 7/2010 | Peters et al. |
| 7,769,462 B2 | 8/2010 | Meadows et al. |
| 7,774,069 B2 | 8/2010 | Olson et al. |
| 7,776,087 B2 | 8/2010 | Aharoni et al. |
| 7,782,190 B1 | 8/2010 | Martin et al. |
| 7,792,588 B2 | 9/2010 | Harding et al. |
| 7,801,615 B2 | 9/2010 | Meadows et al. |
| 7,807,299 B2 | 10/2010 | Howard et al. |
| 7,811,705 B2 | 10/2010 | Scott et al. |
| 7,813,809 B2 | 10/2010 | Strother et al. |
| 7,818,068 B2 | 10/2010 | Meadows et al. |
| 7,839,146 B2 | 11/2010 | Gray |
| 7,848,814 B2 | 12/2010 | Torgerson et al. |
| 7,848,817 B2 | 12/2010 | Janzig et al. |
| 7,865,245 B2 | 1/2011 | Torgerson et al. |
| 7,875,389 B2 | 1/2011 | Scott et al. |
| 7,881,796 B2 | 2/2011 | Scott et al. |
| 7,894,913 B2 | 2/2011 | Boggs, II et al. |
| 7,904,170 B2 | 3/2011 | Harding et al. |
| 7,917,213 B2 | 3/2011 | Bulkes et al. |
| 7,925,357 B2 | 4/2011 | Phillips et al. |
| 7,927,742 B2 | 4/2011 | Scott et al. |
| 7,930,030 B2 | 4/2011 | Woods et al. |
| 7,931,582 B2 | 4/2011 | Forsell |
| 7,932,696 B2 | 4/2011 | Peterson |
| 7,945,334 B2 | 5/2011 | Jimenez et al. |
| 7,952,349 B2 | 5/2011 | Huang et al. |
| 7,962,211 B2 | 6/2011 | Torgerson et al. |
| 7,988,616 B2 | 8/2011 | Forsell |
| 8,005,547 B2 | 8/2011 | Forsberg et al. |
| 8,010,205 B2 | 8/2011 | Rahman et al. |
| RE42,682 E | 9/2011 | Barreras, Sr. et al. |
| 8,024,047 B2 | 9/2011 | Olson et al. |
| 8,036,736 B2 | 10/2011 | Snyder et al. |
| 8,044,635 B2 | 10/2011 | Peterson |
| 8,086,313 B2 | 12/2011 | Singhal et al. |
| 8,096,938 B2 | 1/2012 | Forsell |
| 8,096,939 B2 | 1/2012 | Forsell |
| 8,105,714 B2 | 1/2012 | Schmidt et al. |
| 8,115,448 B2 | 2/2012 | John |
| 8,126,558 B2 | 2/2012 | Forsell |
| 8,140,168 B2 | 3/2012 | Olson et al. |
| 8,147,543 B2 | 4/2012 | Forsell |
| 8,150,529 B2 | 4/2012 | Snell et al. |
| 8,155,752 B2 | 4/2012 | Aghassian et al. |
| 8,162,924 B2 | 4/2012 | Boyden et al. |
| 8,165,663 B2 | 4/2012 | Hyde et al. |
| 8,165,678 B2 | 4/2012 | Forsberg et al. |
| 8,165,692 B2 | 4/2012 | Strother et al. |
| 8,170,681 B2 | 5/2012 | Jimenez et al. |
| 8,175,716 B2 | 5/2012 | Rahman et al. |
| 8,195,304 B2 | 6/2012 | Strother et al. |
| 2003/0171792 A1 | 9/2003 | Zarinetchi et al. |
| 2004/0172102 A1 | 9/2004 | Leysieffer et al. |
| 2004/0173221 A1 | 9/2004 | Singhal et al. |
| 2004/0176815 A1 | 9/2004 | Janzig et al. |
| 2004/0176818 A1 | 9/2004 | Wahlstrand et al. |
| 2005/0075693 A1 | 4/2005 | Toy et al. |
| 2005/0104577 A1 | 5/2005 | Matei et al. |
| 2005/0113887 A1 | 5/2005 | Bauhahn et al. |
| 2006/0183965 A1 | 8/2006 | Kasic |
| 2007/0015959 A1 | 1/2007 | Forsell |
| 2007/0060968 A1 | 3/2007 | Strother et al. |
| 2007/0060980 A1 | 3/2007 | Strother et al. |
| 2007/0066995 A1 | 3/2007 | Strother et al. |
| 2007/0073099 A1 | 3/2007 | Forsell |
| 2007/0150037 A1 | 6/2007 | Hastings et al. |
| 2007/0150038 A1 | 6/2007 | Hastings et al. |
| 2007/0208390 A1 | 9/2007 | Von Arx et al. |
| 2007/0232848 A1 | 10/2007 | Forsell |
| 2007/0233019 A1 | 10/2007 | Forsell |
| 2007/0239224 A1 | 10/2007 | Bennett et al. |
| 2007/0255349 A1 * | 11/2007 | Torgerson et al. ............... 607/61 |
| 2007/0270921 A1 | 11/2007 | Strother et al. |
| 2007/0279020 A1 | 12/2007 | Mozzi et al. |
| 2007/0293914 A1 | 12/2007 | Woods et al. |
| 2008/0020278 A1 | 1/2008 | Schmidt et al. |
| 2008/0021505 A1 | 1/2008 | Hastings et al. |
| 2008/0027500 A1 | 1/2008 | Chen |
| 2008/0044728 A1 | 2/2008 | Schmidt et al. |
| 2008/0051854 A1 | 2/2008 | Bulkes et al. |
| 2008/0092911 A1 | 4/2008 | Schulman et al. |
| 2008/0109054 A1 | 5/2008 | Hastings et al. |
| 2008/0161874 A1 | 7/2008 | Bennett et al. |
| 2008/0177353 A1 | 7/2008 | Hirota et al. |
| 2008/0221555 A1 | 9/2008 | Sheppard et al. |
| 2008/0275296 A1 | 11/2008 | Forsell |
| 2008/0300660 A1 | 12/2008 | John |
| 2009/0018599 A1 | 1/2009 | Hastings et al. |
| 2009/0024179 A1 | 1/2009 | Dronov |
| 2009/0048524 A1 | 2/2009 | Wildau et al. |
| 2009/0054725 A1 | 2/2009 | Forsell |
| 2009/0093713 A1 | 4/2009 | Hyde et al. |
| 2009/0093728 A1 | 4/2009 | Hyde et al. |
| 2009/0112291 A1 | 4/2009 | Wahlstrand et al. |
| 2009/0163964 A1 | 6/2009 | Boyden et al. |
| 2009/0163965 A1 | 6/2009 | Boyden et al. |
| 2009/0163977 A1 | 6/2009 | Boyden et al. |
| 2009/0177139 A1 | 7/2009 | Boyden et al. |
| 2009/0177254 A1 | 7/2009 | Boyden et al. |
| 2009/0182388 A1 | 7/2009 | Von Arx et al. |
| 2009/0216296 A1 | 8/2009 | Meskens et al. |
| 2009/0228077 A1 | 9/2009 | Ginggen et al. |
| 2009/0228078 A1 | 9/2009 | Zhang et al. |
| 2009/0234302 A1 * | 9/2009 | Hoendervoogt et al. 604/288.01 |
| 2009/0240100 A1 | 9/2009 | Forsell |
| 2009/0240294 A1 | 9/2009 | Forsell |
| 2009/0247817 A1 | 10/2009 | Forsell |
| 2009/0247818 A1 | 10/2009 | Forsell |
| 2009/0248109 A1 | 10/2009 | Forsell |
| 2009/0250068 A1 | 10/2009 | Forsell |
| 2009/0254106 A1 | 10/2009 | Forsell |

(56) References Cited

U.S. PATENT DOCUMENTS

| | | |
|---|---|---|
| 2009/0274849 A1 | 11/2009 | Scott et al. |
| 2009/0292336 A1 | 11/2009 | Nishida et al. |
| 2010/0007307 A1 | 1/2010 | Baarman et al. |
| 2010/0063347 A1 | 3/2010 | Yomtov et al. |
| 2010/0106028 A1 | 4/2010 | Penner et al. |
| 2010/0106223 A1 | 4/2010 | Grevious et al. |
| 2010/0137948 A1 | 6/2010 | Aghassian et al. |
| 2010/0145139 A1 | 6/2010 | Forsell |
| 2010/0145412 A1 | 6/2010 | Boyden et al. |
| 2010/0174346 A1 | 7/2010 | Boyden et al. |
| 2010/0210955 A1 | 8/2010 | Forsell |
| 2010/0211091 A1 | 8/2010 | Forsell |
| 2010/0211092 A1 | 8/2010 | Forsell |
| 2010/0217067 A1 | 8/2010 | Forsell |
| 2010/0217295 A1 | 8/2010 | Forsell |
| 2010/0222847 A1 | 9/2010 | Goetz |
| 2010/0228079 A1 | 9/2010 | Forsell |
| 2010/0234792 A1 | 9/2010 | Dacey, Jr. et al. |
| 2010/0234793 A1 | 9/2010 | Dacey, Jr. et al. |
| 2010/0240017 A1 | 9/2010 | Dacey, Jr. et al. |
| 2010/0241048 A1 | 9/2010 | Dacey, Jr. et al. |
| 2010/0241049 A1 | 9/2010 | Dacey, Jr. et al. |
| 2010/0241050 A1 | 9/2010 | Dacey, Jr. et al. |
| 2010/0241051 A1 | 9/2010 | Dacey, Jr. et al. |
| 2010/0241052 A1 | 9/2010 | Dacey, Jr. et al. |
| 2010/0241053 A1 | 9/2010 | Dacey, Jr. et al. |
| 2010/0241054 A1 | 9/2010 | Dacey, Jr. et al. |
| 2010/0241055 A1 | 9/2010 | Dacey, Jr. et al. |
| 2010/0249692 A1 | 9/2010 | Dacey, Jr. et al. |
| 2010/0249888 A1 | 9/2010 | Glenn et al. |
| 2010/0274310 A1 | 10/2010 | Boggs, II et al. |
| 2010/0292629 A1 | 11/2010 | Dacey, Jr. et al. |
| 2010/0305662 A1 | 12/2010 | Ozawa et al. |
| 2010/0305663 A1 | 12/2010 | Aghassian |
| 2010/0316898 A1 | 12/2010 | Howard et al. |
| 2010/0324354 A1 | 12/2010 | Peters et al. |
| 2010/0331917 A1 | 12/2010 | DiGiore et al. |
| 2010/0331918 A1 | 12/2010 | DiGiore et al. |
| 2010/0331919 A1 | 12/2010 | DiGiore et al. |
| 2010/0331920 A1 | 12/2010 | DiGiore et al. |
| 2011/0004269 A1 | 1/2011 | Strother et al. |
| 2011/0015473 A1 | 1/2011 | Forsell |
| 2011/0015474 A1 | 1/2011 | Forsell |
| 2011/0022125 A1 | 1/2011 | Olson et al. |
| 2011/0040143 A1 | 2/2011 | Forsell |
| 2011/0046699 A1 | 2/2011 | Mazanec |
| 2011/0046730 A1 | 2/2011 | Meskens |
| 2011/0054563 A1 | 3/2011 | Janzig et al. |
| 2011/0060386 A1 | 3/2011 | Woods et al. |
| 2011/0066254 A1 | 3/2011 | Forsell |
| 2011/0077720 A1 | 3/2011 | Torgerson et al. |
| 2011/0087337 A1 | 4/2011 | Forsell |
| 2011/0144468 A1 | 6/2011 | Boggs, II et al. |
| 2011/0144566 A1 | 6/2011 | Dacey, Jr. et al. |
| 2011/0152750 A1 | 6/2011 | Dacey, Jr. et al. |
| 2011/0152751 A1 | 6/2011 | Dacey, Jr. et al. |
| 2011/0152752 A1 | 6/2011 | Dacey, Jr. et al. |
| 2011/0152789 A1 | 6/2011 | Dacey, Jr. et al. |
| 2011/0152790 A1 | 6/2011 | Dacey, Jr. et al. |
| 2011/0152978 A1 | 6/2011 | Dacey, Jr. et al. |
| 2011/0160643 A1 | 6/2011 | Dacey, Jr. et al. |
| 2011/0160644 A1 | 6/2011 | Dacey, Jr. et al. |
| 2011/0160681 A1 | 6/2011 | Dacey, Jr. et al. |
| 2011/0166630 A1 | 7/2011 | Phillips et al. |
| 2011/0175568 A1 | 7/2011 | Leijssen et al. |
| 2011/0178576 A1 | 7/2011 | Aghassian |
| 2011/0181238 A1* | 7/2011 | Soar .............................. 320/108 |
| 2011/0184230 A1 | 7/2011 | Forsell et al. |
| 2011/0192402 A1 | 8/2011 | Forsell |
| 2011/0208021 A1 | 8/2011 | Goodall et al. |
| 2011/0208023 A1 | 8/2011 | Goodall et al. |
| 2011/0208026 A1 | 8/2011 | Goodall et al. |
| 2011/0208231 A1 | 8/2011 | Forsell |
| 2011/0218382 A1 | 9/2011 | Orejola |
| 2011/0230930 A1 | 9/2011 | Forsell |
| 2011/0230935 A1 | 9/2011 | Zdeblick |
| 2011/0234155 A1 | 9/2011 | Chen et al. |
| 2011/0273138 A1 | 11/2011 | Baarman et al. |
| 2011/0275912 A1 | 11/2011 | Boyden et al. |
| 2011/0280426 A1 | 11/2011 | Bachler |
| 2011/0281148 A1 | 11/2011 | Scott et al. |
| 2011/0282134 A1 | 11/2011 | Forsell |
| 2011/0288499 A1 | 11/2011 | Forsell |
| 2011/0295088 A1 | 12/2011 | Boyden et al. |
| 2011/0295089 A1 | 12/2011 | Boyden et al. |
| 2011/0295090 A1 | 12/2011 | Boyden et al. |
| 2011/0295159 A1 | 12/2011 | Shachar |
| 2011/0298420 A1* | 12/2011 | Forsberg et al. .............. 320/108 |
| 2011/0301667 A1 | 12/2011 | Olson et al. |
| 2011/0301669 A1 | 12/2011 | Olson et al. |
| 2011/0319703 A1 | 12/2011 | Wiskerke |
| 2011/0319785 A1 | 12/2011 | Snyder et al. |
| 2012/0007441 A1 | 1/2012 | John |
| 2012/0010481 A1 | 1/2012 | Goodall et al. |
| 2012/0012630 A1 | 1/2012 | Lui et al. |
| 2012/0019201 A1 | 1/2012 | Peterson |
| 2012/0032522 A1 | 2/2012 | Schatz et al. |
| 2012/0041285 A1 | 2/2012 | Goodall et al. |
| 2012/0041286 A1 | 2/2012 | Goodall et al. |
| 2012/0041287 A1 | 2/2012 | Goodall et al. |
| 2012/0041515 A1 | 2/2012 | Meskens et al. |
| 2012/0046712 A1 | 2/2012 | Woods et al. |
| 2012/0053657 A1 | 3/2012 | Parker et al. |
| 2012/0101874 A1 | 4/2012 | Ben-Haim et al. |
| 2012/0123505 A1 | 5/2012 | Kothandaraman |
| 2012/0130448 A1 | 5/2012 | Wood et al. |
| 2012/0139485 A1 | 6/2012 | Olson et al. |

* cited by examiner

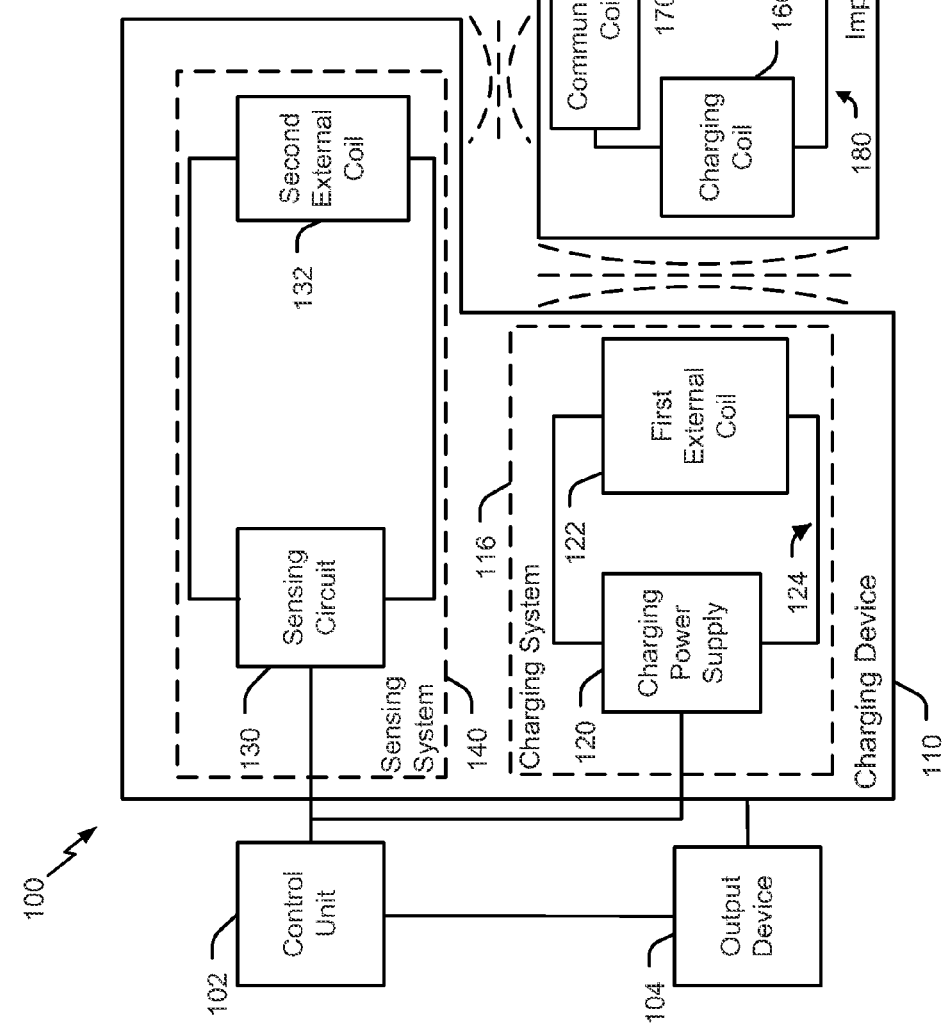
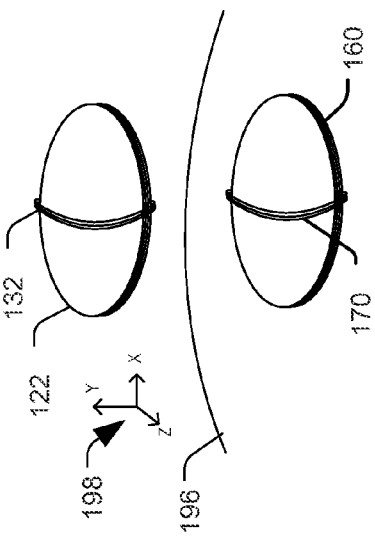
FIG. 1A
FIG. 1B

IMPLANTABLE MEDICAL DEVICE WITH BACKSCATTER SIGNAL BASED COMMUNICATION

FIELD OF THE DISCLOSURE

The present disclosure is generally related to implantable medical devices.

BACKGROUND

Advances in technology have led to the development of small medical devices that can be implanted within a living organism, such as a human, to provide treatment or monitoring. Powering such implantable medical devices may cause some concern. Due to the size of an implantable medical device, an onboard battery may provide a temporary amount of power due to a finite amount of energy that can be stored in the onboard battery. Replacing a battery of the implantable medical device may be expensive and inconvenient. For example, an implantable medical device that is implanted within a human may require invasive surgery to replace the device or to replace the battery of the device. Due to these and other concerns, some implantable medical devices may use rechargeable batteries.

However, charging rechargeable batteries of an implantable medical device may present other concerns. Charging inefficiencies may result in long charging times that may be undesirable for patients and may reduce compliance with a charging procedure. Such inefficiencies may be dependent on various factors that may be associated with use of a charging device to facilitate the charging. Some factors may include alignment, position, and depth of the charging device. The implantable medical device may be unable to communicate information about the implantable medical device to an external device during the charging process due to physical and electrical constraints. For example, the implantable medical device may not be able to communicate with an external device via a communication link because a charging signal may be more powerful than a communication signal, which can cause problems with receiving the communication signal in the presence of the charging signal.

SUMMARY

In a particular embodiment, an implantable medical device includes a charging coil configured to inductively couple to a first external coil to receive a charging signal to charge a charge storage element. The implantable medical device also includes a circuit coupled to the charging coil. The circuit may include a circuit component that, in response to the charging signal, generates a backscatter signal. The implantable medical device also includes a communication coil orthogonal to the charging coil and coupled to the circuit component. The communication coil is configured to inductively couple to a second external coil to communicate the backscatter signal to the second external coil.

In another particular embodiment, a method includes receiving a charging signal at a charging coil of an implantable medical device by inductively coupling the charging coil to a first external coil of a charging device. The method also includes rectifying the charging signal and applying the rectified charging signal to a charge storage element of the implantable medical device. The method includes applying a backscatter signal to a communication coil of the implantable medical device. The backscatter signal may be generated responsive to applying the charging signal to a component coupled to the charging coil. The communication coil may be orthogonal to the charging coil. The method includes sending the backscatter signal to an external device by inductively coupling the communication coil to a second external coil of the external device to communicate the backscatter signal to the second external coil.

In another particular embodiment, a charging device includes a first charging coil configured to couple to a second charging coil of an implantable medical device. The first charging coil may be adapted to communicate a charging signal to the second charging coil to charge a charge storage element of the implantable medical device. The charging device includes a sensing coil that is orthogonal to the first charging coil. The sensing coil may be configured to detect a backscatter signal from a communication coil of the implantable medical device.

In another particular embodiment, a method includes applying a charging signal to a first charging coil of a charging device. The method also includes communicating the charging signal to a second charging coil of an implantable medical device by inductively coupling the second charging coil and the first charging coil. The implantable medical device may include a charge storage element that may be charged using the charging signal. The method also includes detecting, at a sensing coil, a backscatter signal from a communication coil of the implantable medical device. The sensing coil may be orthogonal to the first charging coil.

The features, functions, and advantages of the disclosed embodiments can be achieved independently in various embodiments or may be combined in yet other embodiments, further details of which are disclosed with reference to the following description and drawings.

BRIEF DESCRIPTION OF THE DRAWINGS

FIG. 1A is a block diagram of a particular embodiment of a system including an implantable medical device and a charging device;

FIG. 1B is a diagram of a particular embodiment of the system of FIG. 1A further illustrating an orthogonal arrangement of coils;

Figure 2:
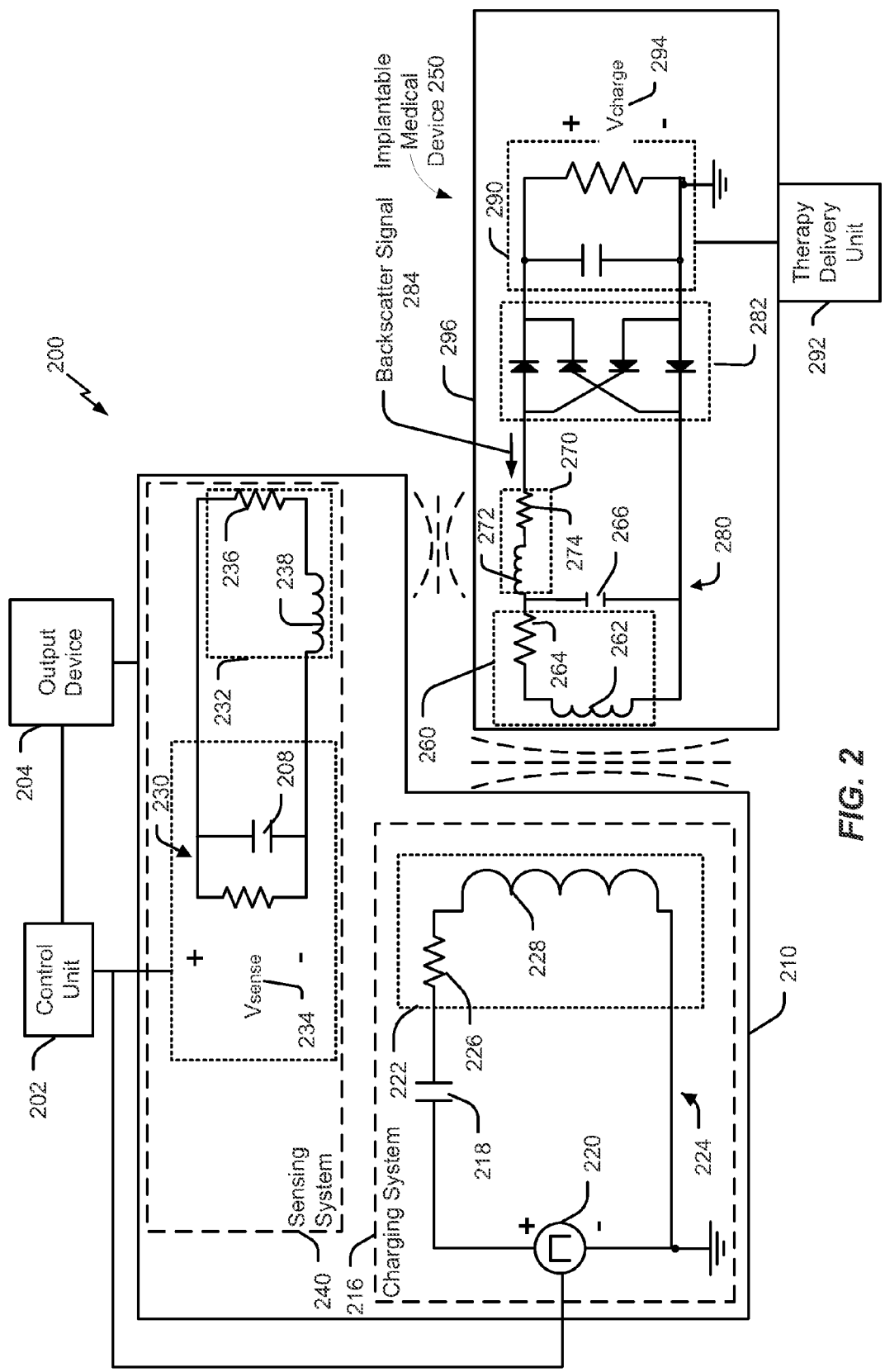
FIG. 2 is a block diagram of a particular embodiment of a system showing circuits within an implantable medical device and a charging device.

Illustrative embodiments are described herein. Particular illustrative embodiments of the present disclosure are described below with reference to the drawings. In the description, common elements are designated by common reference numbers throughout the drawings.

DETAILED DESCRIPTION

An implantable medical device (IMD) may be inductively coupled to an external charging system to receive a charging signal that provides a charge (or a recharge) to a charge storage device (e.g., a rechargeable battery) of the IMD. The external charging system may include a first external coil coupled to an external charging circuit that provides the charging signal to the first external coil from a charging power supply. A charging coil of the IMD may be inductively coupled to the first external coil of the external charging system to enable a transfer of energy via the charging signal. The inductive coupling between the first external coil and the charging coil may cause the charging signal to be received by the charging coil. A circuit component (e.g., a rectifier) coupled to the charging coil may rectify the charging signal to provide a rectified charging signal to the charge storage device of the IMD. The charge storage device may store a charge provided by the rectified charging signal. Thus, inductive coupling between the external charging system and the IMD may enable the charge storage device of the IMD to be wirelessly charged by an external charging system.

In response to producing the rectified charging signal, a backscatter signal may be generated. The backscatter signal may include a harmonic (e.g., a first order harmonic, a second order harmonic, a third order harmonic, or a higher order frequency harmonic) of the charging signal. A communication coil of the IMD may receive the backscatter signal and communicate the backscatter signal to an external device that can process the backscatter signal. The external charging system can be equipped with a sensing circuit including a second external coil that can inductively couple to the communication coil to receive the backscatter signal. A difference in frequency between the backscatter signal and the charging signal may enable both signals to be communicated by different coils within the IMD. To facilitate receipt of the backscatter signal in the presence of the charging signal, the communication coil may be arranged orthogonal to the first external coil.

The sensing circuit may provide the backscatter signal, or data descriptive of or related to the backscatter signal to another component coupled to the sensing circuit, such as a control unit. The control unit may receive and process a measurement of the backscatter signal to determine information regarding the IMD. For example, a peak voltage of the backscatter signal may be related to a peak voltage of the charging signal. The peak voltage of the backscatter signal may be used to determine charging status (e.g., relative charging efficiency and/or charging state) of the charge storage device of the IMD. Receipt of the backscatter signal and/or a measurement of the backscatter signal may be used to detect a presence (i.e., within a patient) of the IMD. Measurements based on the backscatter signal can provide a basis for adjusting the external charging system, the IMD, or both, to improve the charging efficiency of the charging signal. For example, the measurements of the backscatter signal associated with the charging signal can be used to adjust a frequency of the charging signal provided to the IMD. In another example, the measurements of the backscatter signal associated with the charging signal can be used to adjust a position or alignment of the external charging system relative to the IMD to promote charging efficiency. In another example, periodic measurements of the backscatter signal associated with the charging signal can be used to adjust a frequency of the charging signal provided to the IMD to compensate for changes in the position or alignment of the external charging system relative to the IMD during recharge.

By adding the communication coil to the IMD to enable communication of the backscatter signal to an external device, communication hardware (e.g., a communication link) that may otherwise consume space within the IMD and that may depend on energy provided by the charge storage device of the IMD can be reduced or removed entirely. The addition of the communication coil may reduce the area within the IMD that is occupied by communication hardware, thereby reducing an overall weight and size of the IMD.

Referring to FIG. 1A, a particular embodiment of a system 100 including an implantable medical device (IMD) 150 and a charging device 110 is depicted. The system 100 illustrates a particular arrangement of the charging device 110 and the IMD 150 to enable transfer of energy from the charging device 110 to the IMD 150 via inductive coupling. The energy transferred to the IMD 150 may be stored at a charge storage element 190 of the IMD 150. FIG. 1A also illustrates a particular arrangement of the charging device 110 and the IMD 150 to enable the charging device 110 to receive a backscatter signal 184 communicated from the IMD 150 via inductive coupling.

In a particular embodiment, the charging device 110 may include a charging system 116 and a sensing system 140. In other particular embodiments of the system 100, the charging system 116 and the sensing system 140 may be components of separate devices. The charging system 116 may include a first external coil 122 that is coupled to a charging power supply 120. The charging power supply 120 may provide a charging signal to the first external coil 122 via a charging circuit 124 of the charging device 110.

In a particular embodiment, the implantable medical device 150 may include a circuit 180 coupled to a charging coil 160 and a communication coil 170. The circuit 180 includes a circuit component 182 (e.g., a rectifier). The IMD 150 may also include a charge storage element 190 (e.g., a battery, a rechargeable battery, a capacitor, or another charge storage device) that is coupled to the circuit component 182. The charge storage element 190 may store energy that can be used to operate the IMD 150.

The charging coil 160 may be configured to be inductively coupled to the first external coil 122 of the charging system 116 to receive a charging signal communicated by the first external coil 122. The charge storage element 190 may receive a modified (e.g., rectified) charging signal from the circuit component 182. The modified charging signal may provide charge to the charge storage element 190. Thus, the charge storage element 190 may be recharged by the modified charging signal. The modified charging signal may be a rectified charging signal and the circuit component 182 may include a rectifier that rectifies the charging signal to produce the rectified charging signal. In a particular embodiment, the circuit component 182 is or includes a circuit element that does not have a linear relationship between current and voltage of the circuit 180 (also referred to herein as a non-linear circuit element). For example, the non-linear circuit element may include one or more diodes. In a particular embodiment, the circuit component 182 may include one or more diodes that may be arranged to rectify the charging signal to produce the rectified charging signal. In another particular embodiment, the circuit 180 may include a rectifier that includes one or more diodes arranged to rectify the charging signal to produce the rectified charging signal.

The IMD 150 may be adapted to be implanted within a patient to provide therapy, to monitor one or more conditions of the patient, for another purpose, or a combination thereof. In a particular embodiment, the IMD 150 may include one or more therapy delivery units 192 configured to deliver therapy to the patient in which the IMD 150 is implanted. The therapy delivery unit 192 may be coupled to the charge storage element 190 to obtain energy from the charge storage element 190 to deliver the therapy to the patient. The therapy delivery unit 192 may provide sensing, treatment, communication, other functions of the implantable medical device 150, or any combination thereof using the energy obtained from the charge storage element 190. In a particular embodiment, the therapy delivery unit 192 may be a stimulation unit that is configured to deliver the therapy to the patient by application of one or more electrical signals to tissue of the patient. For example, the one or more electrical signals may be applied to the tissue of the patient via one or more electrodes that may be coupled to the therapy delivery unit 192. The tissue may include neural tissue, such as brain tissue or nerve tissue. Nerve tissue may include cranial nerves, such as the vagus nerve, the trigeminal nerve, the hypoglossal nerve, and the glossopharyngeal nerve. In another particular embodiment, the therapy delivery unit may include a drug pump that is configured to deliver a chemical to the patient. In another particular embodiment, the therapy delivery unit 192 may be configured to sense or detect a body parameter of the patient. The therapy delivery unit 192 may be configured to adjust delivery of the therapy to the patient based at least in part on the sensed body parameter. In another particular embodiment, the therapy delivery unit 192 may be adapted to communicate or may be coupled to communication hardware to communicate information to an external device regarding delivery of the therapy to the patient or the sensed body parameter. The therapy delivery unit 192 may be adapted to receive communication of the one or more electrical signals applied to the patient. Note that the term "patient" is used broadly to include any organism and is not intended to imply that the patient is human; although the patient is a human patient in one embodiment.

The communication coil 170 may be positioned within the IMD 150 to receive a backscatter signal 184 produced in response to rectifying the charging signal. In a particular embodiment, the backscatter signal 184 may be produced by the circuit component 182 in response to rectifying the charging signal. In another particular embodiment, one or more components of the IMD 150 (e.g., a housing of the IMD 150 or the charge storage element 190) may cause the backscatter signal 184 to be generated in response to the charging signal. In a particular embodiment, the backscatter signal 184 may have a frequency that is three times the frequency of the charging signal. In another particular embodiment, the backscatter signal 184 may have a frequency that is five times the frequency of the charging signal.

In a particular embodiment, the communication coil 170 may be arranged or positioned orthogonally to the first external coil 122, the charging coil 160, or both, to reduce parasitic inductive coupling between the communication coil 170 and the first external coil 122, the charging coil 160, or both. Such parasitic inductive coupling could cause the charging signal communicated by the first external coil 122 to be received by the communication coil 170 causing the communication coil 170 to communicate a portion of the charging signal, thereby interfering with communication of the backscatter signal 184. FIG. 1B illustrates a particular embodiment of an orthogonal arrangement of coils. In FIG. 1B, the second external coil 132 is wound around the first external coil 122, and both are positioned external to a patient 196. The communication coil 170 is wound around the charging coil 160. The first external coil 122 and the charging coil 160 may each be wound around an axis that is substantially parallel to a y-axis of a coordinate system 198. The communication coil 170 and the second external coil 132 may each be wound around an axis that is substantially parallel to the x-axis of the coordinate system 198. Since the y-axis and the x-axis are orthogonal to one another, the coils used for charging (i.e., the first external coil 122 and the charging coil 160) are said to be arranged orthogonally to the coils used for sensing (i.e., the communication coil 170 and the second external coil 132). As used herein, orthogonal arrangement of the coils is intended to include minor variations, e.g., due to manufacturing constraints or errors. Accordingly, each use of the term orthogonal is understood to mean substantially orthogonal or orthogonal within manufacturing limitations.

One or more external coils (e.g., a second external coil 132) may be inductively coupled with the communication coil 170 to receive the backscatter signal 184. For example, the sensing system 140 may be inductively coupled to the IMD 150 to receive the backscatter signal 184. The sensing system 140 may include the second external coil 132 (e.g., a sensing coil) that may be coupled to a sensing circuit 130. In a particular embodiment, another component coupled to the sensing circuit 130, such as a control unit 102, may receive and process the backscatter signal 184 from the sensing circuit 130 to determine information regarding the IMD 150. The sensing system 140 may be positioned in proximity to the IMD 150 to enable inductive coupling between the second external coil 132 and the communication coil 170.

The backscatter signal 184 may be useful for determining various types of information about of the IMD 150. For example, the control unit 102 may determine a measurement of the backscatter signal 184, which may be used to detect a presence (i.e., within the patient) of the IMD 150 or to determine a relative location of the IMD 150 proximate to the charging device 110. The charging device 110 may be adjusted based on information obtained about the IMD 150 from the backscatter signal 184. The measurement of the backscatter signal 184 may indicate a charging status or relative charging efficiency of the IMD 150 with respect to the charging signal received from the charging device 110. Based on information obtained from the backscatter signal 184, the control unit 102 may adjust the charging system 116 to improve the charging efficiency of the charging signal at the IMD 150.

The control unit 102 may be operably coupled to or may include one or more processors and memory that may be accessible to the one or more processors. The memory may include tangible, non-transitory, computer-readable media (e.g., one or more computer memory devices). The memory may include various memory devices, such as registers, cache, volatile memory, and non-volatile memory. For example, the memory can include cache that is accessible by the processor to rapidly retrieve and store data. The memory can include any data storage device that can store data which can thereafter be read by the processor or by any other computing system. Examples of computer-readable media that the memory may use include, but are not limited to: magnetic media such as hard disks, floppy disks, and magnetic tape; optical media such as CD-ROM disks; magneto-optical media; and specially configured hardware devices such as application-specific integrated circuits (ASICs), programmable logic devices (PLDs), and ROM and RAM devices. The memory may store instructions that are executable by the one or more processors to perform functions of the control unit 102. Additionally or in the alternative, the control unit 102 may be operably coupled to one or more dedicated hardware devices, such as application specific integrated circuits, programmable logic arrays and other hardware devices, to implement the functions of the control unit 102. Accordingly, the present disclosure encompasses software, firmware, and hardware implementations.

An output device 104 may be included in or operably coupled to the charging device 110. Alternatively, the output device 104 may be included in or operably coupled to the control unit 102. The output device 104 may output information received about the charging device 110, the IMD 150, or both. The output device 104 may indicate a measurement of the backscatter signal 184 or charging measurements associated with charging of the IMD 150. The output device may provide information indicating the presence of the IMD 150 within the patient, the relative location of the IMD 150, alignment information indicating alignment (or relative alignment) between the charging device 110 and the IMD 150, or a combination thereof.

The charging signal may be adjusted in response to information determined about the IMD 150 based on the backscatter signal 184. For example, the control unit 102 may control the charging system 116, the sensing system 140, or both, in response to information obtained from processing the backscatter signal 184. The charging signal may be modified in response to determining that a charge stored at the charge storage element 190 satisfies charging criteria (e.g., a charging efficiency threshold or a charge threshold). For example, the control unit 102 may be operable to cause the charging system 116 to perform one or more frequency sweeps of the charging signal to identify, based on the backscatter signal 184, a particular frequency associated with an improved charging efficiency relative to other frequencies of the charging signal. To illustrate, a frequency sweep of the charging signal may be performed to find a particular charging frequency at which the backscatter signal voltage peaks. The peak voltage of the backscatter signal corresponds to a resonant frequency of the charging circuit 124 at a particular time (e.g., while the first external coil 122 and the charging coil 160 have a particular spatial relationship, while the charge storage element 190 has a particular charge level, etc.). The charge efficiency should be at a maximum at the resonant frequency of the charging circuit 124. The frequency of the charging signal may be changed from time to time as conditions change. For example, the inductive coupling between the first external coil 122 and the charging coil 160 may change if the spatial relationship of the charging device 110 and the IMD 150 changes or as the impedance of the charge storage element 190 changes during recharge. The control unit 102 may select a new frequency of the charging signal in response to detecting the change based on the backscatter signal 184.

In a particular embodiment, the IMD 150 may include a conductive housing that at least partially surrounds or encloses components of the IMD 150. The charging coil 160, the circuit 180, the circuit component 182, the charge storage element 190, the communication coil 170, the therapy delivery unit 192, other components of the IMD 150, or a combination thereof, may be enclosed within the conductive housing.

In operation, the charging power supply 120 may be activated to cause the charging signal to be applied to the first external coil 122 via the charging circuit 124. The charging device 110 may be positioned at a location proximate to the IMD 150 to cause the charging coil 160 to be inductively coupled to the first external coil 122. The charging coil 160 may receive the charging signal from the first external coil 122 in response to inductive coupling between the first external coil 122 and the charging coil 160. The charging signal may be provided, via the circuit 180, to the circuit component 182. The circuit component 182 may rectify the charging signal to provide a rectified charging signal. The rectified charging signal may be provided to the charge storage element 190, which may store energy responsive to the rectified charging signal. Thus, the charging device 110 located proximate to the IMD 150 may enable a charge to be wirelessly provided to the IMD 150.

The backscatter signal 184 may be generated by the circuit component 182 in response to the charging signal. The communication coil 170 may receive the backscatter signal 184. The second external coil 132 may receive the backscatter signal 184 from the communication coil 170 via inductive coupling between the communication coil 170 and the second external coil 132. The sensing circuit 130 may receive the backscatter signal 184 from the second external coil 132. The control unit 102 may receive the backscatter signal 184 or data descriptive of the backscatter signal 184 from the sensing circuit 130. The control unit 102 may process the backscatter signal 184 or the data descriptive of the backscatter signal 184 to determine information about the IMD 150. The control unit 102 may control operation of the charging system 116 to adjust the charging signal based on the determined information about the IMD 150. For example, the control unit 102 may adjust the frequency of the charging signal to improve charging efficiency based on the backscatter signal 184.

Thus, the backscatter signal 184 enables wireless communication of information about operation and/or status of the IMD 150. Communication via the backscatter signal 184 does not consume power from the charge storage element 190 of the IMD 150. The IMD 150 may communicate information via the backscatter signal 184 while the IMD 150 is charging the charge storage element 190. Further, cost and maintenance of the IMD 150 can be reduced, because sensing can be performed externally at the sensing system 140 without active communication hardware being present in the IMD 150.

Referring to FIG. 2, a block diagram of a particular embodiment of a system 200 is shown. The system 200 includes an IMD 250 and a charging device 210. The system 200 illustrates circuits within the IMD 250 and the charging device 210 to enable transfer of energy from the charging device 210 to the IMD 250. The system 200 also illustrates circuits within the IMD 250 and the charging device 210 to communicate a backscatter signal 284 to the charging device 210 via inductive coupling with the IMD 250.

The charging device includes a charging system 216. The charging system 216 may include or correspond to the charging system 116 of FIG. 1A. The charging system 216 may include a charging circuit 224 that may include a charging power supply 220, a capacitor 218, and a first charging coil 222. The charging circuit 224 may include or correspond to the charging circuit 124 of FIG. 1A. The charging power supply 220 may include or correspond to the charging power supply 120 of FIG. 1A. The first charging coil 222 may include or correspond to the first external coil 122 of FIG. 1A. In a particular embodiment, the first charging coil 222 may be formed using a first conductor (e.g., a conductive wire). Thus, the first charging coil 222 may exhibit resistance (illustrated in the circuit diagram as a resistor 226) and inductance (illustrated in the circuit diagram as an inductor 228). The charging circuit 224 may include or may be modeled as a resistive (R), inductive (L), and capacitive (C) circuit (also referred to as an "RLC circuit"). An RLC circuit has a resonant frequency, which corresponds to a frequency at which impedance due to inductance and impedance due to capacitance is at a minimum. The resonant frequency is thus an efficient frequency at which to operate the RLC circuit since losses due to inductance and capacitance are reduced or removed. Another characteristic of the resonant frequency of an RLC circuit is that, at the resonant frequency, current and voltage of a signal applied to the RLC circuit are in phase.

In a particular embodiment, the charging circuit 224 may be designed to have a resonant frequency of approximately 10 KHz. Operating at the resonant frequency of 10 KHz may enable improved charging efficiency of the charging signal. The charging power supply 220 may apply a charging signal to the first charging coil 222. Inductive coupling between the first charging coil 222 and another coil may induce currents at the first charging coil 222, thereby causing the resonant frequency of the charging circuit 224 to change. Thus, an actual resonant frequency of the charging circuit 224 may be dynamic and may change over time as a result of interaction between the charging circuit 224 and the IMD 250. In a particular embodiment, an input waveform provided at the charging power supply 220 to generate the charging signal may be a square waveform; however, other input waveforms may be used. In another particular embodiment, the charging circuit 224 may be a narrow-band circuit with a high quality factor (Q) to maintain efficiency of the charging circuit 224, such as maintaining absolute voltage of the charge signal, which may support charging efficiency of the charging signal.

The IMD 250 may include or correspond to the IMD 150 of FIG. 1A. The IMD 250 may include a conductive housing 296 that at least partially surrounds or encloses components of the IMD 250. The IMD 250 may include a circuit 280 that may include a capacitor 266, a second charging coil 260, a communication coil 270, and a circuit component 282. The circuit 280 may include or correspond to the circuit 180 of FIG. 1A. The IMD 250 may also include a charge storage element 290 (e.g., a battery, a rechargeable battery, a capacitor, or another charge storage device) that is coupled to the circuit component 282.

The second charging coil 260 may include or correspond to the charging coil 160 of FIG. 1A. In a particular embodiment, the second charging coil 260 may be formed using a conductor (e.g. a conductive wire). To illustrate, the second charging coil 260 may be wound inside the IMD 250 around a core that may include or enclose one or more components of the IMD 250.

The second charging coil 260 may be configured to receive the charging signal via inductive coupling with the first charging coil 222. The second charging coil 260 may exhibit resistance (illustrated in the circuit diagram as a resistor 264) and inductance (illustrated in the circuit diagram as an inductor 262). The circuit 280 may include or may be modeled as an RLC circuit. In a particular embodiment, the circuit 280 may be designed to operate with a resonant frequency of approximately 10 KHz. The resonant frequency of 10 KHz may enable a greater charging efficiency of the charging signal.

The charge storage element 290 may receive a modified (e.g., rectified) charging signal from the circuit component 282. For example, the modified charging signal may be a rectified charging signal, and the circuit component 282 may include a rectifier that rectifies the charging signal to produce the rectified charging signal. The modified charging signal may provide charge to the charge storage element 290. Thus, the charge storage element 290 may be recharged by the modified charging signal. The charge storage element 290 may store energy that can be used to operate the IMD 250. An amount of charge held by the charge storage element 290 may correspond to a voltage, $V_{charge}$ 294, measured across the charge storage element 290. In a particular embodiment, the charge storage element 290 may include or correspond to the charge storage element 190 of FIG. 1A.

The IMD 250 may be adapted to be implanted within a patient to provide therapy, to monitor one or more conditions of the patient, for another purpose, or a combination thereof. The IMD 250 may include one or more therapy delivery units 292 configured to deliver therapy to the patient in which the IMD 250 is implanted. The therapy delivery unit 292 may correspond to the therapy delivery unit 192 of FIG. 1A. The therapy delivery unit 292 may be coupled to the charge storage element 290 to obtain energy from the charge storage element 290 for operation of the therapy delivery unit 292.

The communication coil 270 may exhibit resistance (illustrated in the circuit diagram as a resistor 274) and inductance (illustrated in the circuit diagram as an inductor 272). In a particular embodiment, the communication coil 270 may be formed using a conductor (e.g., conductive wire). The communication coil 270 may be configured to receive the backscatter signal 284 via the circuit 280.

The communication coil 270 may be arranged or positioned orthogonal to the second charging coil 260. In a particular embodiment, the communication coil 270 may be wound around the core of the IMD 250. The orthogonal arrangement of the coils is described with reference to FIG. 1B. As an example of an orthogonal arrangement of the coils of FIG. 2, the communication coil 270 and the sensing coil 232 may be wound around axes that are parallel to a first axis of a coordinate system, and the first charging coil 222 and the second charging coil 260 may be wound around axes that are parallel to a second axis of the coordinate system. The first axis of the coordinate system and the second axis of the coordinate system may be orthogonal, or substantially orthogonal, to each other. Thus, the communication coil 270 and the sensing coil 232 may be said to be orthogonal to the first charging coil 222 and the second charging coil 260. Positioning the communication coil 270 orthogonal to the second charging coil 260 may reduce an amount of parasitic inductive coupling that may occur between the communication coil 270 and the second charging coil 260, the first charging coil 222, or both.

In a particular embodiment, the conductor (e.g., conductive wire) used to form the communication coil 270 has less volume, less mass, or both, than the conductor used to form the second charging coil 260. For example, a smaller quantity (e.g., shorter length) of a thinner conductive wire may be used to form the communication coil 270 than a conductor used to form the second charging coil 260. Thus, the communication coil 270 may have a low impact on space, weight, or both, of the IMD 250 when added to the IMD 250 to enable communication of the backscatter signal 284. The backscatter signal 284 may be communicated efficiently when the communication coil 270 has an inductance of about 35 uH (e.g., approximately 10-50 uH). The communication coil 270 may be configured to have a lower Q and a broader band than the second charging coil 260. The broader band of the communication coil 270 allows the backscatter signal 284 to be communicated to the second external coil 232 without significant attenuation from the communication coil 270 even if the frequency of the backscatter signal 284 changes. The conductor used to form the communication coil 270 may be more lossy than the conductor used to form the second charging coil 260 resulting in a lower Q and broader band for the communication coil 270. Lossiness of the communication coil 270 and reception of the backscatter signal 284 at a broad-band circuit of the sensing system 240 may facilitate communication of the backscatter signal 284 at a higher frequency (e.g., third or fifth order harmonics of the charging signal frequency) and may reduce impact of the second charging coil 260 and the first charging coil 222 on communication of the backscatter signal 284. Because the communication coil 270 is formed to enable the backscatter signal 284 to be received at a frequency greater than the frequency of the first charging coil 222 and the second charging coil 260, the communication coil 270 may not receive the charging signal, which may be at a lower frequency.

The sensing system 240 may include or correspond to the sensing system 140 of FIG. 1A. The sensing system 240 may include the sensing circuit 230 that includes a capacitor 208 and that may be coupled to a sensing coil 232. The sensing coil 232 may exhibit resistance (illustrated in the circuit diagram as a resistor 236) and inductance (illustrated in the circuit diagram as an inductor 238). In a particular embodiment, the sensing coil 232 may be formed using a conductor (e.g., conductive wire). In a particular embodiment, the sensing coil 232 may be arranged or positioned orthogonal to the first charging coil 222 and the second charging coil 260, and may be position or arranged parallel to (e.g., in alignment with) the communication coil 270. Parasitic coupling that could occur between the sensing coil 232 and the second charging coil 260, the first charging coil 222, or both may be reduced by orthogonal arrangement. The sensing coil 232 may be configured to receive the backscatter signal 284. In a particular embodiment, the backscatter signal 284 may be communicated efficiently when the sensing coil 232 has an inductance of about 75 uH (e.g., 60-100 uH). The sensing coil 232 may be configured to have a lower Q and a broader band than the first charging coil 222. The broader band of the sensing coil 232 allows the backscatter signal 284 to be received without significant attenuation even if the frequency of the backscatter signal 284 changes as the charging signal frequency is adjusted or swept to find the resonant frequency of the charging circuit 224. The conductor used to form the sensing coil 232 may be more lossy than the conductor used to form the first charging coil 222 resulting in a lower Q and broader band for the sensing coil 232. The backscatter signal 284 may be communicated to the sensing coil 232 at a higher frequency (e.g., third or fifth order harmonics of the charging signal frequency), which may reduce impact of the second charging coil 260 and the first charging coil 222 on communication of the backscatter signal 284. Because the sensing coil 232 is formed to enable the backscatter signal 284 to be received at a frequency greater than the frequency of the first charging coil 222 and the second charging coil 260, sensing coil 232 may not receive the charging signal, which may be at a lower frequency.

The sensing circuit 230 may detect a characteristic of the backscatter signal, such as a sensed voltage, $V_{sense}$ 234. The sensing circuit 230 may provide the backscatter signal 284, or data descriptive of or related to the backscatter signal 284 (such as a value of $V_{sense}$ 234) to another component coupled to the sensing circuit 230, such as a control unit 202. The control unit 202 may be coupled to the sensing circuit 230 to obtain the value of $V_{sense}$ 234 or another measured characteristic of the backscatter signal 284. In a particular embodiment, the value of $V_{sense}$ 234 may be related to or indicative of a value of $V_{charge}$ 294. For example, the value of $V_{sense}$ 234 may track the value of $V_{charge}$ 294. The peak value of $V_{charge}$ 294, which indicates maximum charge efficiency, may correspond to a peak value of $V_{sense}$ 234. Thus, a frequency sweep of the charging signal may be performed while the value of $V_{sense}$ 234 is measured in order to determine a frequency of the charging signal that corresponds to a peak value of $V_{sense}$ 234 and therefore, an improved charging rate or an improved charging efficiency with respect to the charge storage element 290.

The control unit 202 may correspond to the control unit 102 of FIG. 1A. The control unit 202 may receive and process the backscatter signal 284 or data descriptive of the backscatter signal 284 from the sensing circuit 230 to determine information regarding the IMD 250. The control unit 202 may control the charging system 216, the sensing system 240, or both, in response to information obtained from processing the backscatter signal 284.

An output device 204 may be included in or operably coupled to the charging device 210. Alternatively, the output device 204 may be included in or operably coupled to the control unit 202. The output device 204 may output information received about the charging device 210, the IMD 250, or both. For example, the output device 204 may provide a visual, audible or haptic output that is indicative of a measured characteristic of the backscatter signal 284 (e.g., $V_{sense}$ 234) or is indicative of estimated information associated with charging of the IMD 250 (e.g., $V_{charge}$ 294, a rate of change of $V_{charge}$ 294, relative charging efficiency of the charging signal, etc.). The output device may provide information indicating the presence of the IMD 250 within the patient, the relative location of the IMD 250, alignment information indicating alignment between the charging device 210 and the IMD 250, or a combination thereof.

In a particular embodiment, a measured value of $V_{sense}$ 234 may be used to identify a concern associated with the charge storage element 290. For example, when the charge storage element 290 is unable to store charge provided by the rectified charging signal, the measured value of $V_{sense}$ 234 may be less than an expected value of $V_{sense}$ 234. To illustrate, when a load of the charge storage element 290 is opened such that the rectified charging signal applied to the charge storage element cannot be stored, the backscatter signal 284 may be affected such that $V_{sense}$ 234 may be significantly lower, or zero.

In a particular embodiment, the measured value of $V_{sense}$ 234 may be used to determine when to cease providing the charging signal to the IMD 250. In a particular embodiment, the circuit 280 of the IMD 250 may include a switch that controls distribution of the charging signal based on a temperature of the IMD 250. For example, the switch may open (creating an opening in the circuit 280) when a temperature of the conductive housing 296 reaches a temperature threshold. The open switch may prevent the charging signal from being rectified to apply the rectified charging signal to the charge storage element 290. The backscatter signal 284 may be affected such that the measured value of $V_{sense}$ 234 is reduced. The reduced value of $V_{sense}$ 234 may indicate that the charge storage element 290 is not storing charge. In a particular embodiment, when the value of $V_{sense}$ 234 falls below a charging threshold, the charging device 210 may cease application of the charging signal to the first charging coil 222 to cease communication of the charging signal to the IMD 250. During recharge, the impedance of the charge storage element 290 may change. The changes in impedance, the amount of time the charge storage element 290 has been charging, or a combination thereof, may be used to determine the state of the charge storage element 290. In some embodiments, the backscatter frequency is periodically or continuously measured to identify impedance changes to track, or determine, the charging state of the charge storage element 290. Periodic or continuous frequency sweeps of the charging signal may also be performed during charging to monitor the peak value of $V_{sense}$ 234. The frequency of the charging signal may need to be adjusted if the peak value of $V_{sense}$ 234 changes with the impedance of the charge storage element 290.

Thus, communication of the backscatter signal from the IMD to an external device may enable the external device to obtain information about the IMD while the IMD is charging without consuming energy from the charge storage element. A measurement of the backscatter signal may provide an indication of operation and/or status of the IMD, which can be used to adjust the charging device to improve charging efficiency of the IMD in response to the charging signal.

Figure 3:
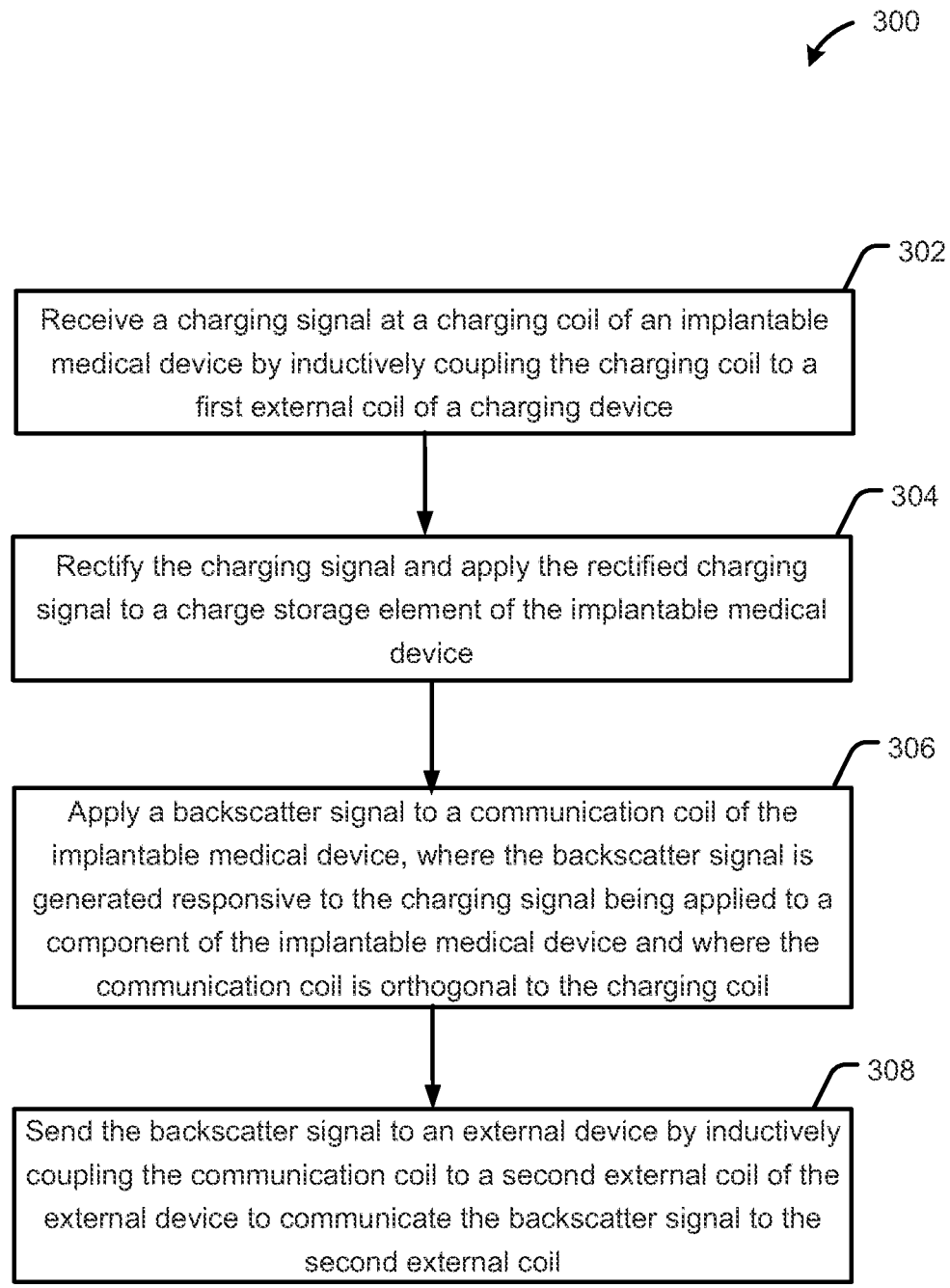
FIG. 3 is flow chart of a particular embodiment of a method of communicating a backscatter signal from an implantable medical device to an external device.

FIG. 3 is flow chart of a particular embodiment of a method 300 of communicating a backscatter signal from an implantable medical device to an external device. For example, the method 300 may be performed by an implantable medical device, such as the IMD 150 of FIG. 1A or the IMD 250 of FIG. 2.

At 302, the method 300 may include receiving a charging signal at a charging coil of the implantable medical device by inductively coupling the charging coil to a first external coil of a charging device. For example, the charging coil 160 of the IMD 150 of FIG. 1A may receive a charging signal by inductive coupling of the charging coil 160 and the first external coil 122 of the charging device 110. In another example, the second charging coil 260 of the IMD 250 of FIG. 2 may receive a charging signal by inductive coupling of the second charging coil 260 and the first charging coil 222. In a particular embodiment, the inductive coupling between the first external coil and the charging coil may affect the resonant frequency of the charging circuit of the charging device, which may reduce the efficiency of charge provided to the IMD. The frequency at which the charging signal is transferred to the first external coil may be adjusted to accommodate the effects of the inductive coupling. Periodic or continuous frequency sweeps of the charging signal may be performed during charging to monitor the peak value of $V_{sense}$ 234. The frequency of the charging signal may be adjusted based on changes in the peak value of $V_{sense}$ 234 that may be caused by inductive coupling, alignment issues, or any combination thereof.

At 304, the method 300 may include rectifying the charging signal and applying the rectified charging signal to a charge storage element of the implantable medical device. For example, the circuit component 182 of FIG. 1A may rectify the charging signal received from the charging coil 160. The circuit component 182 may provide the rectified charging signal to the charge storage element 190. The current provided by the rectified charging signal may cause the charge storage element 190 to store charge.

At 306, the method 300 may include applying a backscatter signal to a communication coil of the implantable medical device, where the backscatter signal is generated responsive to the charging signal being applied to a component of the implantable medical device and where the communication coil is orthogonal to the charging coil. For example, the IMD 150 of FIG. 1A may apply the backscatter signal 184 to the communication coil 170 of the IMD 150. To illustrate, the circuit component 182 of the IMD 150 may generate the backscatter signal 184 in response to application of the charging signal to a component of the implantable medical device (e.g., the circuit component 182). To mitigate parasitic inductive coupling between the communication coil 170 and the charging coil 160, the first external coil 122, or both, the communication coil 170 may be positioned orthogonally to the charging coil 160.

At 308, the method 300 may also include sending the backscatter signal to an external device by inductively coupling the communication coil to a second external coil of the external device to communicate the backscatter signal to the second external coil. For example, the communication coil 170 of FIG. 1A may send the backscatter signal 184 to the charging device 110 by inductively coupling the communication coil 170 to the second external coil 132 to communicate the backscatter signal 184 to the second external coil 132. In another example, the communication coil 270 of FIG. 2 may send the backscatter signal 284 to the charging device 210 by inductively coupling the communication coil 270 to the sensing coil 232 to communication the backscatter signal 284 to the sensing coil 232.

Thus, the backscatter signal can be communicated to a device external to the IMD to provide information about the IMD. Placing the communication coil orthogonal to the charging coil may reduce inductive coupling between these coils. As explained above, inductive coupling between the communication coil and the second external coil facilitates communication between the IMD and the external device without consumption of energy from the charge storage element of the IMD.

Figure 4:
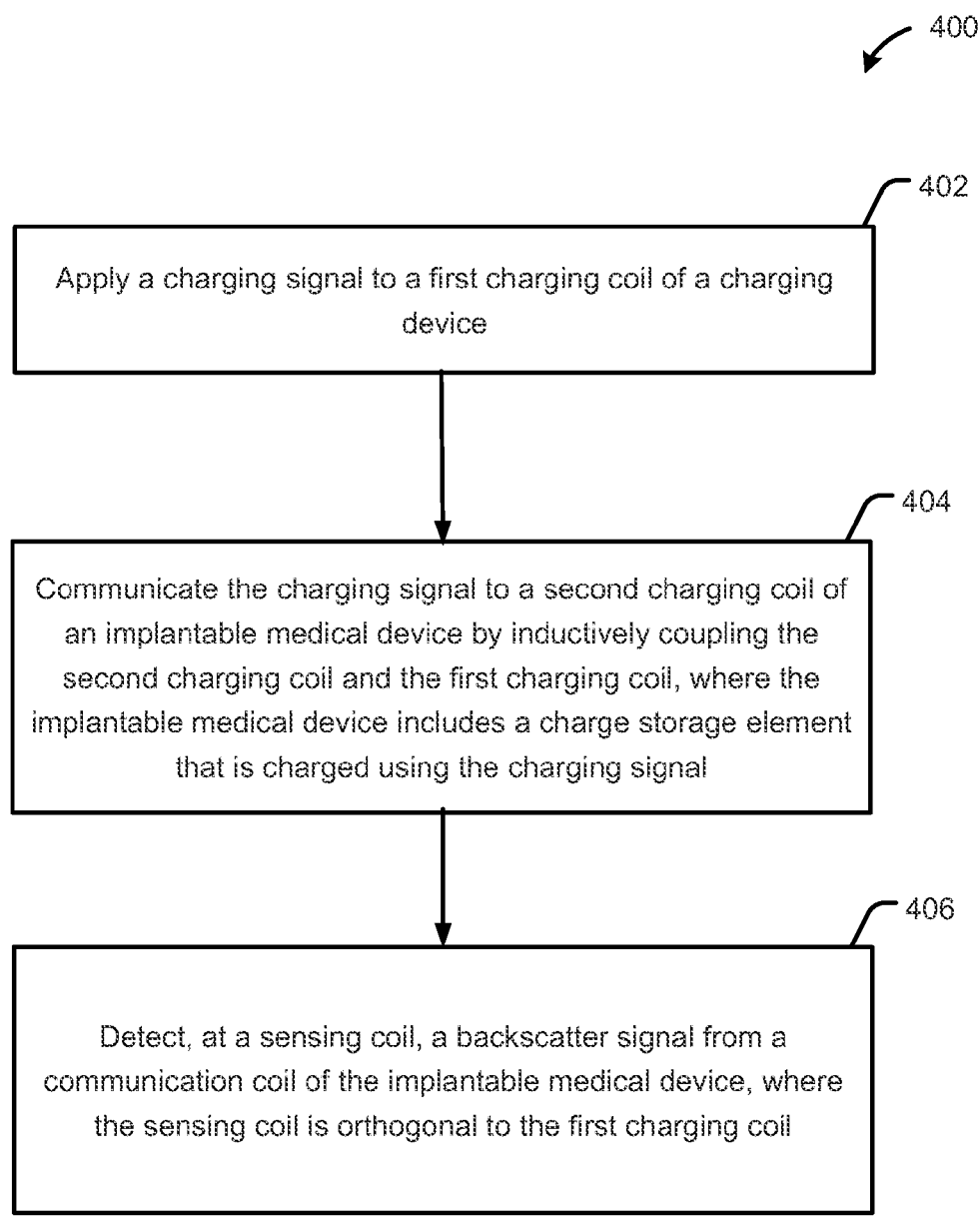
FIG. 4 is a flow chart of a first embodiment of a method of detecting a backscatter signal sent from an implantable medical device.

FIG. 4 is a flow chart of a first embodiment of a method 400 of detecting a backscatter signal received from an implantable medical device in response to application of a charging signal to the implantable medical device. For example, the method 400 may be performed by the charging device 110 of FIG. 1A. In another example, the method may be performed by the charging device 210 of FIG. 2.

At 402, the method 400 includes applying a charging signal to a first charging coil of a charging device. For example, the charging device 110 of FIG. 1A may apply a charging signal to the first external coil 122. In a particular embodiment, the charging device may be coupled to logic or configured to control application of the charging signal. In a particular embodiment, the charging signal may be provided to the first charging coil at or near a resonant frequency of a circuit of the charging device.

At 404, the method 400 also includes communicating the charging signal to a second charging coil of an implantable medical device by inductively coupling the second charging coil and the first charging coil, where the implantable medical device includes a charge storage element that is charged using the charging signal. For example, the charging device 110 of FIG. 1A may communicate a charging signal to the second charging coil 160 of the IMD 150 by inductively coupling the charging coil 160 and the first external coil 122. The IMD 150 may charge the charge storage element 190 based on the charging signal. Efficiency of energy transfer of the charging signal via inductive coupling may be related to position, distance, and alignment between the IMD 150 and the charging device 110 and other factors.

At 406, the method 400 includes detecting, at a sensing coil, a backscatter signal from a communication coil of the implantable medical device, where the sensing coil is orthogonal to the first charging coil. For example, the second external coil 132 of FIG. 1A may detect the backscatter signal 184 from the communication coil 170. To reduce parasitic effects on the inductive coupling between the first external coil 122 and the charging coil 160, the second external coil 132 may be positioned orthogonally to the first external coil 122.

Detecting the backscatter signal at the external device may enable wireless communication of information about the implantable medical device to the external device without consumption of energy from the charge storage element of the implantable medical device. The backscatter signal 184 from the communication coil 170 may be at a different frequency from the charging signal frequency, such as a third or fifth harmonic of the charging signal frequency. The charging circuit 124 of the charging device 110 may be a narrow band circuit and be unaffected by the higher frequency backscatter signal 184. Furthermore, the first external coil 122 may be substantially orthogonal to both the communication coil 170 and the second external coil 132 to further minimize interference so that charging and backscatter communication may occur concurrently. Therefore, the external device may obtain the information from the backscatter signal 184 without changing or affecting an external charging system that transfers energy to the implantable medical device via inductive coupling. Additionally, the addition of the communication coil may have little impact on volume, weight, or both, of the implantable medical device.

Figure 5:
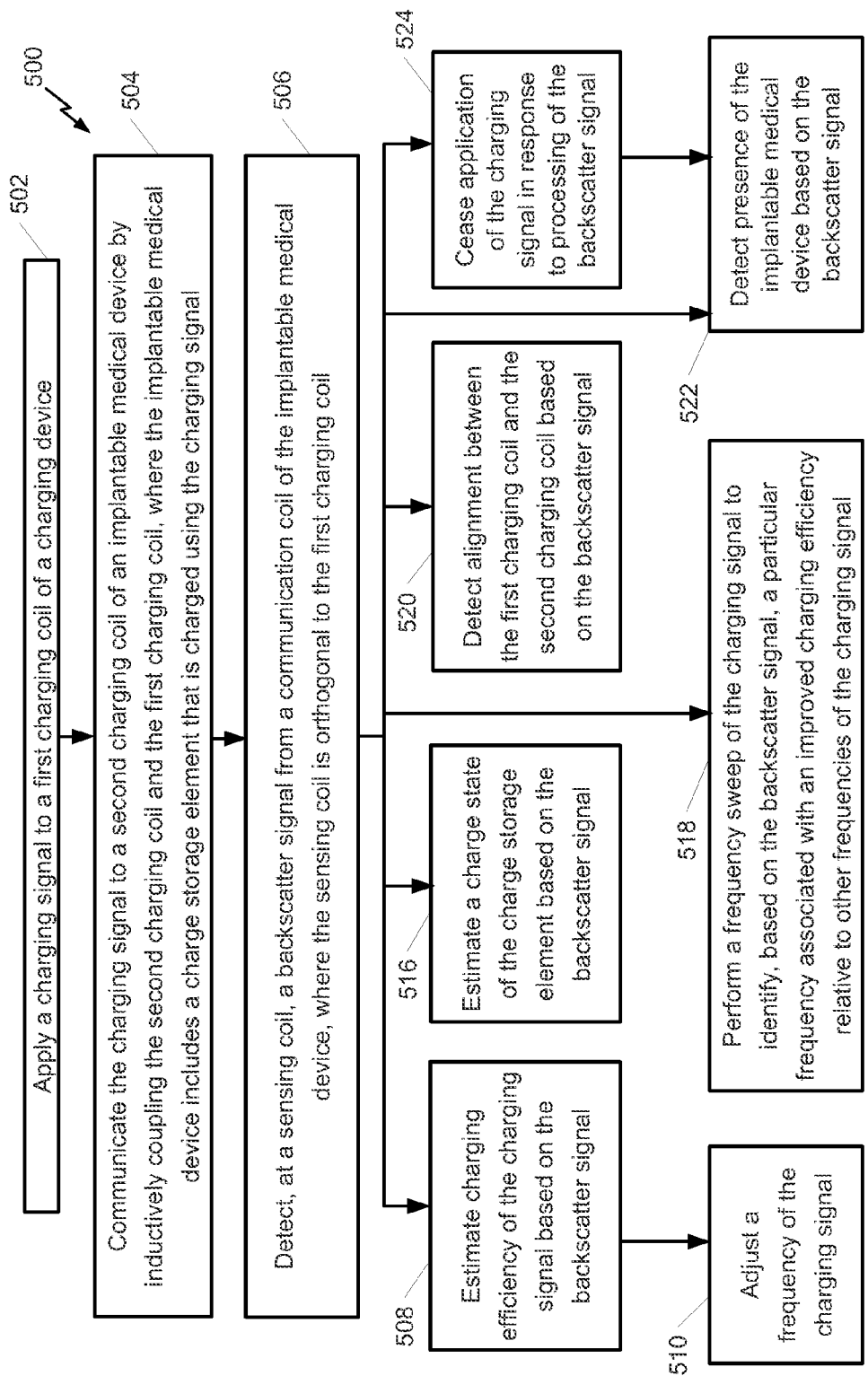
FIG. 5 is a flow chart of a second embodiment of a method of detecting a backscatter signal from an implantable medical device.

FIG. 5 is a flow chart of a second embodiment of a method 500 of detecting a backscatter signal received from an implantable medical device in response to application of a charging signal to the implantable medical device. For example, the method 500 may be performed by the charging device 110 of FIG. 1A. In another example, the method may be performed by the charging device 210 of FIG. 2.

At 502, the method 500 includes applying a charging signal to a first charging coil of a charging device. For example, the charging device 210 of FIG. 2 may apply a charging signal to the first charging coil 222. In a particular embodiment, the charging device may be coupled to logic or configured to control application of the charging signal to the first charging coil. In a particular embodiment, the charging signal may be provided to the first charging coil at or near a resonant frequency of a circuit of the charging device.

At 504, the method 500 also includes communicating the charging signal to a second charging coil of an implantable medical device by inductively coupling the second charging coil and the first charging coil, where the implantable medical device includes a charge storage element that is charged using the charging signal. For example, the charging device 210 of FIG. 2 may communicate a charging signal to the second charging coil 260 of the IMD 250 by inductively coupling the second charging coil 260 and the first charging coil 222. The IMD 250 may charge the charge storage element 290 based on the charging signal.

At 506, the method 500 includes detecting, at a sensing coil, a backscatter signal from a communication coil of the implantable medical device, where the sensing coil is orthogonal to the first charging coil. For example, the sensing coil 232 of FIG. 2 may detect the backscatter signal 284 from the communication coil 270.

At 508, the method 500 may include estimating a charging efficiency of the charging signal based on the backscatter signal. For example, the charging device 210 of FIG. 2 may estimate a charging efficiency of the charging signal based on the backscatter signal 284. In a particular embodiment, the control unit 202 may estimate the charging efficiency. The charging efficiency may be based at least in part on a measured value of $V_{sense}$ 234 obtained from the sensing circuit 230. Analysis of $V_{sense}$ 234 may be used to determine charging information associated with the charge storage element 290, such as a charging rate. The charging rate may provide an indication of the charging efficiency. Charging efficiency may be estimated based at least in part on a comparison of the charging rate to an expected or ideal charging rate.

At 510, the method 500 may include adjusting a frequency of the charging signal to improve charging efficiency of the charging signal. For example, the frequency of the charging signal may be adjusted based at least in part on the estimated charging efficiency. To illustrate, the control unit 202 of FIG. 2 may cause the charging power supply 220 to adjust the frequency of the charging signal.

At 516, the method 500 may include estimating a charge state of the charge storage element based on the backscatter signal. For example, the charging device 210 of FIG. 2 may estimate the charge state of the charge storage element 290 based on the backscatter signal 284. The charge state may be indicative of a quantity of energy stored at the charge storage element. To illustrate, the charge state may correspond to a voltage across the charge storage element. In a particular embodiment, the control unit 202 may estimate the charge state of the charge storage element 290 based on the backscatter signal 284. For example, a measured value of $V_{sense}$ 234 may be used to estimate the charge state of the charge storage element 290.

At 518, the method 500 may include performing a frequency sweep of the charging signal to identify, based on the backscatter signal, a particular frequency associated with an improved charging efficiency relative to other frequencies of the charging signal. For example, the charging device 210 of FIG. 2 may perform a frequency sweep of the charging signal to identify, based on the backscatter signal, a particular frequency associated with an improved charging efficiency relative to other frequencies of the charging signal. For example, the charging device 210 may determine one or more estimates of the charging efficiency of the IMD 250 for one or more frequencies identified during the frequency sweep of the charging signal. The charging device 210 may determine a particular frequency from the one or more frequencies that corresponds to an improved charging efficiency relative to other charging efficiencies of the one or more frequencies. For example, the sensing system 240 may be configured to detect and measure a voltage $V_{sense}$ 234 corresponding to the backscatter signal 284 at each charging signal frequency applied to the IMD 250 during the frequency sweep. The peak value of $V_{sense}$ 234 resulting from the frequency sweep may be indicative of a peak value of the charging voltage $V_{charge}$ 294. The peak value of $V_{sense}$ 234 may be indicative of a frequency of the charging signal that provides improved charging efficiency because the charging efficiency is at maximum when $V_{charge}$ 294 is at its peak. Therefore, the charging signal frequency providing a backscatter signal with the peak value of $V_{sense}$ 234 may correspond to the frequency with an improved charging efficiency relative to other frequencies of the charging signal. Periodic or continuous frequency sweeps of the charging signal may be performed during charging to monitor the peak value of $V_{sense}$ 234. The frequency of the charging signal may be adjusted based on changes in the peak value of $V_{sense}$ 234 during charging.

At 520, the method 500 includes detecting alignment between the first charging coil and the second charging coil based on the backscatter signal. For example, the charging device 210 of FIG. 2 may detect alignment between the first charging coil 222 and the second charging coil 260 based on the backscatter signal 284. In a particular embodiment, the control unit 202 associated with the charging device 210 may detect the alignment between the first charging coil 222 and the second charging coil 260 based on the backscatter signal 284. The charging device 210 may determine one or more estimates of charging efficiency of the IMD 250 as the charging device is aligned at one or more positions and while the first charging coil 222 maintains inductive coupling with the second charging coil 260 and the communication coil 270 maintains inductive coupling with the sensing coil 232. At a particular position, the charging device 210 may detect alignment between the first charging coil 222 and the second charging coil 260 based on a characteristic of the backscatter signal 284 (e.g., a peak in the value of $V_{sense}$ 234). The charging device 210 may be moved to alternate positions until the charging device 210 detects alignment between the first charging coil 222 and the second charging coil 260.

At 522, the method 500 may include detecting presence of the implantable medical device based on the backscatter signal. For example, the charging device 210 of FIG. 2 may detect the presence of the IMD 250 based on the backscatter signal 284. In a particular embodiment, the control unit 202 may detect a presence of the IMD 250 based on the backscatter signal 284. For example, the presence of the IMD 250 may be detected when a value of $V_{sense}$ 234 is measured at the sensing circuit 230. In a particular embodiment, a detection threshold may be defined, such that the charging device 210 may determine that the IMD 250 is present when the value of $V_{sense}$ 234 satisfies the detection threshold.

At 524, the method 500 may include ceasing application of the charging signal in response to processing of the backscatter signal. For example, the charging device 210 of FIG. 2 may cease application of the charging signal in response to processing of the backscatter signal 284. In a particular embodiment, the control unit 202 may cease application of the charging signal in response to processing of the backscatter signal 284. A threshold voltage may be defined such that the charging device 210 may stop application of the charging signal to the first charging coil 222 when the threshold voltage is not satisfied. The threshold voltage may be a voltage that indicates that the charge storage element 290 is not storing charge from the charging signal when the first charging coil 222 is inductively coupled to the second charging coil 260 and the communication coil 270 is inductively coupled to the sensing coil 232. In some embodiments, the threshold voltage may be a fixed value, a percentage of the peak value of the sensed voltage $V_{sense}$ 234, or a value that changes depending on the charging state of the charge storage element 290.

In another particular embodiment, information determined based on the backscatter signal may be used to cease application of the charging signal. For example, a portion of energy of the charging signal that does not result in charging of the charge storage element 290 of FIG. 2 may be lost as heat, which may increase a temperature of the IMD 250. To limit temperature rise of the IMD 250 to a level that is safe to be in contact with the tissue of the patient, the charging system 216 may cease application of the charging signal to the IMD 250 based on information related to temperature rise of the IMD 250, such as a time of application of the charging signal and the estimated charging efficiency of the charging signal. In another example, the charging system 216 may determine, based on a characteristic of the backscatter signal 284, that the charge storage element 290 is not storing charge and may cease application of the charging signal to the IMD 250 in response to the determination. To illustrate, a measured value of $V_{sense}$ 234 may indicate that the charge storage element 290 of FIG. 2 is not storing charge. The IMD 250 may be equipped with an automatic switch to shutoff charging at the charge storage element 290 when a temperature threshold of the IMD 250 is exceeded. Thus, when the IMD 250 automatically stops charging of the charge storage element 290, the charging device 210 may automatically cease application of the charging signal.

Figure 6A:
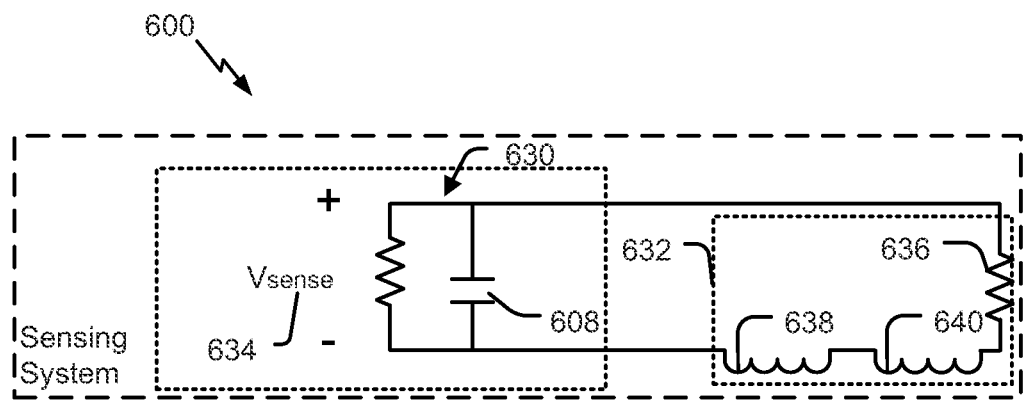
FIG. 6A is a block diagram of a particular embodiment of a sensing system of a charging device.

Referring to FIG. 6A, a particular embodiment of a sensing system 600 of a charging device 110 is depicted. An external sensing coil 632 may be inductively coupled with the communication coil 170 of FIG. 1A to receive the backscatter signal 184. For example, the sensing system 600 may be inductively coupled to the IMD 150 of FIG. 1A to receive the backscatter signal 184. The sensing system 600 may include the external sensing coil 632 that may be coupled to a sensing circuit 630. In a particular embodiment, another component coupled to the sensing circuit 630, such as a control unit, may receive and process the backscatter signal 184 from the sensing circuit 630 to determine information regarding the IMD 150. The sensing circuit 630 may detect a characteristic of the backscatter signal, such as a sensed voltage, $V_{sense}$ 634. The sensing system 600 may be positioned in proximity to the IMD 150 to enable inductive coupling between the sensing coil 632 and the communication coil 170.

Figure 6B:
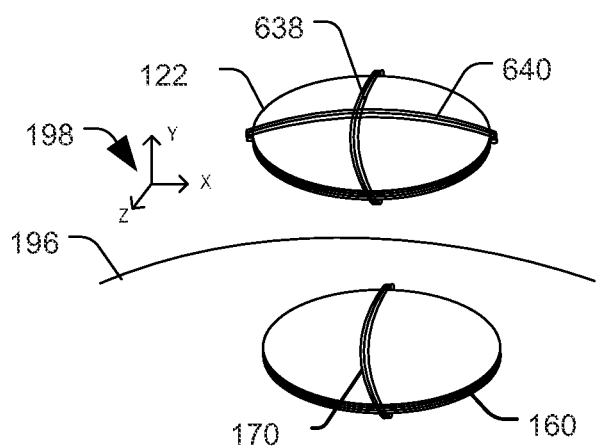
FIG. 6B is a diagram of a particular embodiment of the system of FIG. 6A further illustrating an orthogonal arrangement of coils.

The sensing circuit 630 may include a capacitor 608 and that may be coupled to the sensing coil 632. The sensing coil 632 may exhibit resistance (illustrated in the circuit diagram as a resistor 636). The sensing coil 632 may exhibit inductance depicted by two inductors in series, a first inductor 638 representing a first portion of the sensing coil 632, and a second inductor 640 representing a second portion of the sensing coil 632. The first and second inductors, 638 and 640, may also be substantially orthogonal to one another as illustrated in FIG. 6B. In a particular embodiment, both the first inductor 638 and the second inductor 640 of the sensing coil 632 may be arranged or positioned orthogonal to the first charging coil 122 and the second charging coil 160. The alignment of the sensing coil 632 with the communication coil 170 will depend on the rotational position of the external charging device 110. In FIG. 1B, when the rotational position of the charging device 110 is such that the communication coil 170 and the second external coil 132 are substantially orthogonal, the backscatter signal may be very difficult to sense at the sensing system 140. Returning to FIGS. 6A-6B, to minimize the sensitivity of the charging device 110 to rotational misalignment, the sensing coil 632 may include the two orthogonally placed inductors 638 and 640 as illustrate in FIG. 6B. When the rotational position of the external charging device 110 is such that the first inductor 638 is substantially orthogonal to the communication coil 170, the second inductor 640 will be substantially parallel with the communication coil 170 and be able to sense the backscatter signal 184. In this configuration, regardless of the rotational position of the charging device 110, at least one of the two orthogonally placed inductors 638 and 640 should be able to sense the backscatter signal 184.

Although the description above contains many specificities, these specificities are utilized to illustrate some particular embodiments of the disclosure and should not be construed as limiting the scope of the disclosure. The scope of this disclosure should be determined by the claims and their legal equivalents. A method or device does not have to address each and every problem to be encompassed by the present disclosure. All structural, chemical and functional equivalents to the elements of the disclosure that are known to those of ordinary skill in the art are expressly incorporated herein by reference and are intended to be encompassed by the present claims. A reference to an element in the singular is not intended to mean one and only one, unless explicitly so stated, but rather it should be construed to mean at least one. No claim element herein is to be construed under the provisions of 35 U.S.C. §112, sixth paragraph, unless the element is expressly recited using the phrase "means for." Furthermore, no element, component or method step in the present disclosure is intended to be dedicated to the public, regardless of whether the element, component or method step is explicitly recited in the claims.

The disclosure is described above with reference to drawings. These drawings illustrate certain details of specific embodiments of the systems and methods and programs of the present disclosure. However, describing the disclosure with drawings should not be construed as imposing on the disclosure any limitations that may be present in the drawings. The present disclosure contemplates methods, systems and program products on any machine-readable media for accomplishing its operations. The embodiments of the present disclosure may be implemented using an existing computer processor, a special purpose computer processor, or by a hardwired system.

As noted above, embodiments within the scope of the present disclosure include program products including machine-readable media for carrying or having machine-executable instructions or data structures stored thereon. Such machine-readable media can be any available media which can be accessed by a general purpose or special purpose computer or other machine with a processor. By way of example, such machine-readable media can include RAM, ROM, EPROM, EEPROM, CD ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. The disclosure may be utilized in a non-transitory media. When information is transferred or provided over a network or another communications connection (either hardwired, wireless, or a combination of hardwired or wireless) to a machine, the machine properly views the connection as a machine-readable medium. Thus, any such connection is properly termed a machine-readable medium. Combinations of the above are also included within the scope of machine-readable media. Machine-executable instructions include, for example, instructions and data which cause a general purpose computer, a special purpose computer, or special purpose processing machines to perform a certain function or group of functions.

Embodiments of the disclosure are described in the general context of method steps which may be implemented in one embodiment by a program product including machine-executable instructions, such as program code, for example, in the form of program modules executed by machines in networked environments. Generally, program modules include routines, programs, objects, components, data structures, etc., that perform particular tasks or implement particular abstract data types. Machine-executable instructions, associated data structures, and program modules represent examples of program code for executing steps of the methods disclosed herein. The particular sequence of such executable instructions or associated data structures represent examples of corresponding acts for implementing the functions described in such steps.

Embodiments of the present disclosure may be practiced in a networked environment using logical connections to one or more remote computers having processors. Logical connections may include a local area network (LAN) and a wide area network (WAN) that are presented here by way of example and not limitation. Such networking environments are commonplace in office-wide or enterprise-wide computer networks, intranets and the Internet and may use a wide variety of different communication protocols. Those skilled in the art will appreciate that such network computing environments will typically encompass many types of computer system configurations, including personal computers, hand-held devices, multi-processor systems, microprocessor-based or programmable consumer electronics, network PCs, servers, minicomputers, mainframe computers, and the like. For example, the network computing environment may include the control unit 102 of FIG. 1A, the one or more therapy delivery units 192, the control unit 202 of FIG. 2, the one or more therapy delivery units 292, or any combination thereof. Embodiments of the disclosure may also be practiced in distributed computing environments where tasks are performed by local and remote processing devices that are linked (either by hardwired links, wireless links, or by a combination of hardwired or wireless links) through a communications network. In a distributed computing environment, program modules may be located in both local and remote memory storage devices.

An exemplary system for implementing the overall system or portions of the disclosure might include a general purpose computing device in the form of a computer, including a processing unit, a system memory, and a system bus that couples various system components including the system memory to the processing unit. For example, the general purpose computing device may include the control unit 102 of FIG. 1A, the one or more therapy delivery units 192, the control unit 202 of FIG. 2, and the one or more therapy delivery units 292. The system memory may include read only memory (ROM) and random access memory (RAM). The computer may also include a magnetic hard disk drive for reading from and writing to a magnetic hard disk, a magnetic disk drive for reading from or writing to a removable magnetic disk, and an optical disk drive for reading from or writing to a removable optical disk such as a CD ROM or other optical media. The drives and their associated machine-readable media provide nonvolatile storage of machine-executable instructions, data structures, program modules, and other data for the computer.

It should be noted that although the flowcharts provided herein show a specific order of method steps, it is understood that the order of these steps may differ from what is depicted. Also two or more steps may be performed concurrently or with partial concurrence. Such variation will depend on the software and hardware systems chosen and on designer choice. It is understood that all such variations are within the scope of the disclosure.

The foregoing description of embodiments of the disclosure has been presented for purposes of illustration and description. It is not intended to be exhaustive or to limit the disclosure to the precise form disclosed, and modifications and variations are possible in light of the above teachings or may be acquired from practice of the disclosure. The embodiments were chosen and described in order to explain the principals of the disclosure and its practical application to enable one skilled in the art to utilize the disclosure in various embodiments and with various modifications as are suited to the particular use contemplated.

The Abstract of the Disclosure is submitted with the understanding that it will not be used to interpret or limit the scope or meaning of the claims. In addition, in the foregoing Detailed Description, various features may be grouped together or described in a single embodiment for the purpose of streamlining the disclosure. This disclosure is not to be interpreted as reflecting an intention that the claimed embodiments require more features than are expressly recited in each claim. Rather, as the following claims reflect, the claimed subject matter may be directed to less than all of the features of any of the disclosed embodiments.

What is claimed is:
1. An implantable medical device comprising:
   a charging coil configured to inductively couple to a first external coil to receive a charging signal to charge a charge storage element;
   a circuit coupled to the charging coil, the circuit including a circuit component that, in response to the charging signal being applied to the circuit, generates a backscatter signal having a higher frequency than the charging signal; and
   a communication coil orthogonal to the charging coil and coupled to the circuit component, the communication coil configured to inductively couple to a second external coil to communicate the backscatter signal to the second external coil.

2. The implantable medical device of claim 1, wherein the circuit component includes a non-linear circuit element.

3. The implantable medical device of claim 1, wherein the circuit includes a rectifier and wherein the circuit component includes a diode of the rectifier.

4. The implantable medical device of claim 1, further comprising a therapy delivery unit configured to be coupled to the charge storage element, the therapy delivery unit configured to be implanted into a patient and to deliver therapy to the patient.

5. The implantable medical device of claim 1, wherein the higher frequency of the backscatter signal is less than five times a frequency of the charging signal.

6. The implantable medical device of claim 1, wherein the higher frequency of the backscatter signal is approximately five times a frequency of the charging signal.

7. The implantable medical device of claim 1, wherein the charging coil is formed from a first conductor wound about a core, wherein the communication coil is formed from a second conductor wound about the core, and wherein the second conductor is more lossy than the first conductor.

8. The implantable medical device of claim 1, wherein the charging coil, the communication coil, and the circuit are included in a device that is configured to be implanted into a patient.

9. The implantable medical device of claim 1, wherein the backscatter signal is indicative of a charging voltage applied to the charge storage element, the charging voltage responsive to the charging signal.

10. A method comprising:
receiving a charging signal at a charging coil of an implantable medical device via inductive coupling of the charging coil to a first external coil of a charging device;
rectifying the charging signal and applying the rectified charging signal to a charge storage element of the implantable medical device;
applying a backscatter signal, having a higher frequency than the charging signal, to a communication coil of the implantable medical device, wherein the backscatter signal is generated responsive to the charging signal being applied to a component of the implantable medical device and wherein the communication coil is orthogonal to the charging coil; and
sending the backscatter signal to an external device by inductively coupling the communication coil to a second external coil of an external device to communicate the backscatter signal to the second external coil.

11. The method of claim 10, wherein the second external coil is orthogonal to the first external coil and the charging coil, and wherein the communication coil is orthogonal to the first external coil.

12. The method of claim 11, wherein the external device is included in the charging device, and wherein the charge storage element comprises a rechargeable battery.

13. The method of claim 10, wherein the backscatter signal is associated with a harmonic frequency of the charging signal.

14. A charging device comprising:
a first charging coil configured to couple to a second charging coil of an implantable medical device, wherein the first charging coil is adapted to communicate a charging signal to the second charging coil to charge a charge storage element of the implantable medical device; and
a sensing coil that is orthogonal to the first charging coil, the sensing coil configured to detect a backscatter signal, having a higher frequency than the charging signal, from a communication coil of the implantable medical device, the backscatter signal generated by the implantable medical device responsive to the charging signal.

15. The charging device of claim 14, wherein the backscatter signal is generated by a component of the implantable medical device responsive to the charging signal being applied to the component of the implantable medical device.

16. The charging device of claim 14, further comprising a control unit configured to perform a frequency sweep of the charging signal.

17. The charging device of claim 14, further comprising a control unit configured to cease application of the charging signal in response to processing of the backscatter signal.

18. The device of claim 14, wherein the sensing coil comprises a first inductor and a second inductor, the first inductor corresponding to a first portion of the sensing coil and a second inductor corresponding to a second portion of the sensing coil, and wherein the first inductor is orientated substantially orthogonal to the second inductor and the first charging coil.

19. A method comprising:
applying a charging signal to a first charging coil of a charging device;
communicating the charging signal to a second charging coil of an implantable medical device by inductively coupling the second charging coil and the first charging coil, wherein the implantable medical device includes a charge storage element that is charged using the charging signal; and
detecting, at a sensing coil, a backscatter signal, having a higher frequency than the charging signal, from a communication coil of the implantable medical device, wherein the sensing coil is orthogonal to the first charging coil, the backscatter signal generated by the implantable medical device responsive to the charging signal.

20. The method of claim 19, further comprising estimating a charging efficiency of the charging signal based on the backscatter signal.

21. The method of claim 20, further comprising, after estimating the charging efficiency, adjusting a frequency of the charging signal.

22. The method of claim 19, further comprising performing a frequency sweep of the charging signal to identify, based on the backscatter signal, a particular frequency associated with an improved charging efficiency relative to other frequencies of the charging signal.

23. The method of claim 19, further comprising ceasing application of the charging signal in response to processing of the backscatter signal.

* * * * *